(12) United States Patent
Nishimura et al.

(10) Patent No.: US 8,883,966 B2
(45) Date of Patent: Nov. 11, 2014

(54) RAB6KIFL/KIF20A EPITOPE PEPTIDE AND VACCINES CONTAINING THE SAME

(75) Inventors: Yasuharu Nishimura, Kumamoto (JP); Katsunori Imai, Kumamoto (JP); Yusuke Nakamura, Tokyo (JP); Takuya Tsunoda, Kanagawa (JP)

(73) Assignee: OncoTherapy Science, Inc., Kanagawa (JP)

( * ) Notice: Subject to any disclaimer, the term of this patent is extended or adjusted under 35 U.S.C. 154(b) by 389 days.

(21) Appl. No.: 13/125,548

(22) PCT Filed: Oct. 15, 2009

(86) PCT No.: PCT/JP2009/005382
§ 371 (c)(1),
(2), (4) Date: Jul. 6, 2011

(87) PCT Pub. No.: WO2010/047062
PCT Pub. Date: Apr. 29, 2010

(65) Prior Publication Data
US 2011/0262471 A1  Oct. 27, 2011

Related U.S. Application Data

(60) Provisional application No. 61/197,106, filed on Oct. 22, 2008.

(51) Int. Cl.
```
A61K 31/00    (2006.01)
A61K 38/00    (2006.01)
A61K 38/04    (2006.01)
C07K 2/00     (2006.01)
C07K 4/00     (2006.01)
C07K 5/00     (2006.01)
C07K 7/00     (2006.01)
C07K 14/00    (2006.01)
C07K 16/00    (2006.01)
C07K 17/00    (2006.01)
G01N 33/00    (2006.01)
G01N 33/48    (2006.01)
A61K 39/00    (2006.01)
C07K 14/47    (2006.01)
C12N 9/14     (2006.01)
```
(52) U.S. Cl.
CPC ............ C07K 14/47 (2013.01); A61K 39/0011 (2013.01); *A61K 2207/15* (2013.01); C12N 9/14 (2013.01); *A01K 2267/0387* (2013.01)
USPC ............... 530/328; 530/300; 436/64; 436/86; 514/1; 514/1.1; 514/19.2; 514/19.3; 514/19.4; 514/19.5

(58) Field of Classification Search
USPC ............ 530/300, 328; 436/64, 86; 514/1, 1.1, 514/19.2, 19.3, 19.4, 19.5
See application file for complete search history.

(56) References Cited

U.S. PATENT DOCUMENTS

| | | |
|---|---|---|
| 6,664,232 B1 | 12/2003 | Itoh et al. |
| 6,783,961 B1 | 8/2004 | Edwards et al. |
| 2003/0194704 A1 | 10/2003 | Penn et al. |
| 2006/0216301 A1 | 9/2006 | Tahara et al. |
| 2009/0175844 A1 | 7/2009 | Nakamura et al. |
| 2009/0252752 A1 | 10/2009 | Tahara et al. |
| 2009/0312264 A1 | 12/2009 | Itoh et al. |
| 2009/0317392 A1 | 12/2009 | Nakamura et al. |
| 2010/0040641 A1 | 2/2010 | Tsunoda et al. |
| 2010/0215676 A1 | 8/2010 | Tahara et al. |
| 2012/0328636 A1 | 12/2012 | Tahara et al. |
| 2013/0028923 A1 | 1/2013 | Tahara et al. |

FOREIGN PATENT DOCUMENTS

| | | |
|---|---|---|
| CN | 1073878 A | 7/1993 |
| CN | 1362263 A | 8/2002 |
| CN | 1469926 A | 1/2004 |
| CN | 1781934 A | 6/2006 |
| CN | 1872877 A | 12/2006 |
| EP | 0546787 A2 | 6/1993 |
| EP | 1983003 A2 | 10/2008 |
| JP | 2007/277251 A | 10/2007 |
| WO | 01/72295 A2 | 10/2001 |
| WO | 02/086443 A2 | 10/2002 |
| WO | 02/102235 A2 | 12/2002 |
| WO | 2004/058153 A2 | 7/2004 |
| WO | 2005/016962 A2 | 2/2005 |
| WO | 2006/038208 A2 | 4/2006 |
| WO | 2006/058496 A1 | 6/2006 |
| WO | 2006/090810 A2 | 8/2006 |
| WO | WO 2006/085684 A2 | 8/2006 |
| WO | 2007/018047 A1 | 2/2007 |
| WO | WO 2007/013665 A2 | 2/2007 |
| WO | WO 2008/102557 A1 | 8/2008 |
| WO | WO 2008/102906 A1 | 8/2008 |

OTHER PUBLICATIONS

Mural et al. A comparison of whole-genome shotgun-derived mouse chromosome 16 and the human genome. Science 296: 1661-1671, May 31, 2002.*

(Continued)

Primary Examiner — Alana Harris Dent
(74) Attorney, Agent, or Firm — Kilpatrick Townsend & Stockton LLP

(57) ABSTRACT

The present invention provides oligopeptides comprising the amino acid sequence selected from the group consisting of SEQ ID NOs: 3, 4 and 5. The present invention also provides a pharmaceutical composition containing the amino acid sequence of selected from the group consisting of SEQ ID NOs: 3, 4 and 5 formulated for the treatment or prevention of cancer in a subject. Furthermore, the present invention provides a method of inducing immune response using such oligopeptides and pharmaceutical agents.

5 Claims, 7 Drawing Sheets

(56) References Cited

OTHER PUBLICATIONS

Kinesin family member 20A, isoform CRA_b [*Mus musculus*]. Jun. 7, 2007.*

Kondo, et al., "Prominent Roles of Secondary Anchor Residues in Peptide Binding to HLA-A24 Human Class I Molecules," *J. Immunol.*, vol. 155(9), pp. 4307-4312 (Nov. 1, 1995).

Database Geneseq, "CD147 binding site for antibody ABX-CBL," retrieved from EBI Accession No. GSP: AAY39470, 1 page (Nov. 19, 1999).

Database Geneseq, "Self-assembling di-block oligopeptide DV20," retrieved from EBI Accession No. GSP: ABP59402, 1 page (Jun. 9, 2003).

Database Geneseq, "Human BH3 peptide #54," retrieved from EBI Accession No. GSP: ASP16103, 1 page (Aug. 21, 2008).

Gross, et al., "High vaccination efficiency of low-affinity epitopes in antitumor immunotherapy," J Clin Invest., vol. 113(3), pp. 425-433 (Feb. 2004).

Suda, et al., "Identification of *secernin 1* as a novel immunotherapy target for gastric cancer using the expression profiles of cDNA microarray," Cancer Sci. May 2006;97(5):411-9.

U.S. Appl. No. 13/464,831, filed May 4, 2012, 163 pages.

Dionne, et al., "Her-2/*neu* altered peptide ligand-induced CTL responses: implications for peptides with increased HLA affinity and T-cell-receptor interaction," *Cancer Immunol Immunother.*, vol. 53(4) pp. 307-314 (Apr. 2004, Epub Nov. 5, 2003).

Hoffman, et al., "The Ability of Variant Peptides to Reverse the Nonresponsiveness of T Lymphocytes to the Wild-Type Sequence P53$_{264-272}$ Epitope," *J Immunol.*, vol. 168(3), pp. 1338-1347 (Feb. 1, 2002).

Zaremba, et al., "Identification of an Enhancer Agonist Cytotoxic T Lymphocyte Peptide from Human Carcinoembryonic Antigen," *Cancer Res.* vol. 57(20), pp. 4570-4577 (Oct. 15, 1997).

Yarilin, Fundamentals of Immunology. Moscow, 1999, pp. 221-223, p. 228, with English translation, 15 pages.

Roitt et al., Immunology, 2000, pp. 196-199, in Russian.

Corresponding English document of Roitt et al., Immunology, pp. 196-199, 2000.

Lee et al., "Increased Vaccine-Specific T Cell Frequency After Peptide-Based Vaccination Correlates with Increased Susceptibility to in Vitro Stimulation but Does Not Lead to Tumor Regression", *J. Immunol.*, 1999, vol. 163, No. 11, pp. 6292-6300.

Roitt et al., Immunology, 2000, pp. 10-13, in Russian.

Corresponding English document of Roitt et al., Immunology, 2000, pp. 10-13.

U.S. Appl. No. 13/536,327, filed Jun. 28, 2012, 204 pgs.

Adams, H-P., et al., "Prediction of binding to MHC class I molecules," *Journal of Immunological Methods*, vol. 185, pp. 181-190 (1995).

Allan, V., et al., "Membrane motors," *Curr Opin Cell Biol.*, vol. 11, pp. 476-482 (1999).

Bachinsky, M., et al., "Mapping and binding analysis of peptides derived from the tumor-associated antigen surviving for eight HLA alleles," *Cancer Immun.*, vol. 5, p. 6, 9 pgs. (Mar. 22, 2005).

Belli, F., et al., "Vaccination of Metastatic Melanoma Patients with Autologous Tumor-Derived heat Shock Protein gp96-Peptide Complexes: Clinical and Immunological Findings," *Journal of Clinical Oncology*, vol. 20(20), pp. 4169-4180 (Oct. 15, 2002).

Boon, T., "Tumor Antigens Recognized by Cytolytic T Lymphocytes: Present Perspectives for Specific Immunotherapy," *Int. J. Cancer*, vol. 54(2), pp. 177-180 (May 8, 1993).

Boon, T., et al., "Human Tumor Antigens Recognized by T Lymphocytes," *J. Exp. Med.*, vol. 183(3), pp. 725-729 (Mar. 1, 1996).

Butterfield, L.H., et al., "Generation of Human T-cell Responses to an HLA-A2.1-restricted Peptide Epitope Derived from α-Fetoprotein," *Cancer Research*, vol. 59(13), pp. 3134-3142 (Jul. 1, 1999).

Coulie, P., et al., "Cytolytic T-Cell responses of cancer patients vaccinated with a MAGE antigen," *Immunol Rev.*, vol. 188, pp. 33-42 (Oct. 2002).

Echard, A., et al., "Interaction of a Golgi-Associated kinesin-Like Protein with Rab6," *Science*, vol. 279(5350), pp. 580-585 (Jan. 23, 1998).

Eloubeidi, M., et al., "Prognostic factors for survival in pancreatic cancer: a population-based study," *The American Journal of Surgery*, vol. 192(3), pp. 322-329 (Sep. 2006).

Fujie, T., et al., "A MAGE-1-Encoded HLA-A24-Binding Synthetic Peptide Induces Specific Anti-Tumor Cytotoxic T Lymphocytes," *Int. J. Cancer*, vol. 80(2), pp. 169-172 (Jan. 18, 1999).

Goonetilleke, K., et al., "Nationwide questionnaire survey of the contemporary surgical management of pancreatic cancer in the United Kingdom & Ireland," *Int. J. Surg.*, vol. 5, pp. 147-151 (2007).

Harada, M., et al., "Kinesin superfamily protein-derived peptides with the ability to induce glioma-reactive cytotoxic T lymphocytes in human leukocyte antigen-A24$^+$ glioma patients," *Oncol Rep.*, vol. 17(3), pp. 629-636 (Mar. 2007).

Harris, C., "Structure and Function of the p53 Tumor Suppressor Gene: Clues for Rational Cancer Therapeutic Strategies," *J. Natl. Cancer Inst.*, vol. 88(20), pp. 1442-1455 (Oct. 16, 1996).

Hirokawa, N., et al., "Kinesin and dynein superfamily proteins in organelle transport and cell division," *Curr Opin Cell Biol.*, vol. 10(1), pp. 60-73 (Feb. 1998).

Imai, K., et al., "Identification of a novel tumor-associated antigen, RAB6KIFL, as a candidate of target for immunotherapy of pancreatic cancer," *Proceedings of the Japanese Society for Immunology*, vol. 38, p. 101, Abstract 1-H-W15-1-O/P (Nov. 5, 2008).

Kikuchi, M., et al., "Identification of a SART-1-Derived Peptide Capable of Inducing HLA-A24-Restricted and Tumor-Specific Cytotoxic T Lymphocytes," *Int. J. Cancer*, vol. 81(3), pp. 459-466 (May 5, 1999).

Kuzushima K., et al., "Efficient identification of HLA-A*2402-restricted cytomegalovirus-specific CD8$^+$ T-cell epitopes by a computer algorithm and an enzyme-linked immunospot assay," *Blood*, vol. 98(6), pp. 1872-1881 (2001).

Lockhart, A.C., et al., "Treatment for Pancreatic Cancer: Current Therapy and Continued Progress, *Gastroenterology*, vol. 128(6), pp. 1642-1654 (May 2005).

Oiso, M., et al., "A Newly Identified MAGE-3-Derived Epitope Recognized by HLA-A24-Restricted Cytotoxic T Lymphocytes," *Int. J. Cancer*, vol. 81(3), pp. 387-394 (May 5, 1999).

Parker, K., et al., "Scheme for Ranking Potential HLA-A2 Binding Peptides Based on Independent Binding of Individual Peptide Side-Chains," *J. Immunol.*, vol. 152(1), pp. 163-175 (1994).

Rosenberg, S., et al., "Cancer immunotherapy: moving beyond current vaccines," *Nat. Med.*, vol. 10(9), pp. 909-915 (Sep. 2004).

Sener, S., et al., "Pancreatic Cancer: A Report of Treatment and Survival Trends for 100,313 Patients Diagnosed from 1985-1995, Using the National Cancer Database," *J. Am. Coll. Surg.*, vol. 189(1), pp. 1-7 (Jul. 1999).

Schueler-Furman, O., et al., "Structure-based prediction of binding peptides to MHC class I molecules: Application to a broad range of MHC alleles," *Protein Science*, vol. 9, pp. 1838-1846 (2000).

Smeenk, H.G., et al., "Survival after surgical management of pancreatic adenocarcinoma: does curative and radical surgery truly exist?," *Langenbecks Arch Surg.*, vol. 390(2), pp. 94-103 (Apr. 2005, Epub May 14, 2004).

Tanaka, F., et al., "Induction of Antitumor Cytotoxic T Lymphocytes with a MAGE-3-encoded Synthetic Peptide Presented by Human Leukocytes Antigen-A24," *Cancer Res.*, vol. 57(20), pp. 4465-4468 (Oct. 15, 1997).

Taniuchi, K., et al., "Down-regulation of RAB6KIFL/KIF20A, a Kinesin Involved with Membrane Trafficking of Discs Large Homologue 5, Can Attenuate Growth of Pancreatic Cancer Cell," *Cancer Res.*, vol. 65(1), pp. 105-112 (Jan. 1, 2005).

Taniuchi, K., et al., "Identification and functional analysis of RAB6KIFL up-regulated in pancreatic cancer," *Nihon Ganciakkai Sokai*, vol. 63, pp. 79, Abstract W-135 (2004).

Van Der Burg, S., et al., "Immunogenicity of Peptides Bound to MHC Class I Molecules Depends on the MHC-Peptide Complex Stability," *J. Immunol.*, vol. 156(9), pp. 3308-3314 (May 1, 1996).

(56) References Cited

OTHER PUBLICATIONS

Vissers, J., et al., "The Renal Cell Carcinoma-associated Antigen G250 Encodes a Human Leukocyte Antigen (HLA)-A2.1-restricted Epitope Recognized by Cytotoxic T Lymphocytes," *Cancer Res.*, vol. 59(21), pp. 5554-5559 (Nov. 1, 1999).

Yeo, C., et al., "Pancreaticoduodenectomy for Cancer of the Head of the Pancreas," *Annals of Surgery*, vol. 221(6), pp. 721-731 (1995).

U.S. Appl. No. 13/168,720, filed Jun. 24, 2011 (204 pgs.).

Dionne, et al., "Functional characterization of CTL against gp100 altered peptide ligands," *Cancer Immunol Immunother.*, vol. 52(4), pp. 199-206 (Apr. 2003, Epub Feb. 18, 2003).

Falk, et al., "Allele-specific motifs revealed by sequencing of self-peptides eluted from MHC molecules," *Nature*, vol. 351(6324), pp. 290-296 (May 23, 1991).

Kondo, et al., "Prominent Roles of Secondary Anchor Residues in Peptide Binding to HLA-A24 Human Class I Molecules," *J. Immunol.* vol. 155(9), pp. 4307-4312 (Nov. 1, 1995).

Kubo, et al., "Definition of Specific Peptide Motifs for Four Major HLA-A Alleles," *J Immunol.*, vol. 152(8), pp. 3913-3924 (Apr. 15, 1994).

Rammensee, et al., "MHC ligands and peptide motifs: first listing," *Immunogenetics*, vol. 41(4), pp. 178-228.

U.S. Appl. No. 14/274,373, filed May 9, 2014, 123 pages.

U.S. Appl. No. 13/744,354, filed Jan. 17, 2013, 124 pages.

U.S. Appl. No. 14/079,144, filed Nov. 13, 2013, 159 pages.

Baldueva et al., "Antitumor Vaccines", Prakticheskaya Onkologiya, 4(3):157-166 (2003), with English translation, 18 pages.

\* cited by examiner

| Various malignancies | n | Positive rate (%) | Relative expression ratio (mean) |
|---|---|---|---|
| Pancreatic cancer | 6 | 100 | 31892 |
| Small cell lung cancer | 15 | 100 | 22 |
| Bladder cancer | 31 | 97 | 20471 |
| Non-small cell lung cancer | 22 | 91 | 25779 |
| Cholangiocellular carcinoma | 11 | 64 | 3781 |
| Breast cancer | 61 | 44 | 322 |
| Prostate cancer | 36 | 31 | 4 |
| Renal cell carcinoma | 11 | 27 | 5 |
| Esophageal cancer | 13 | 15 | 3 |
| Colorectal cancer | 31 | 3 | 2 |
| Gastric cancer | 4 | 0 | 0 |

A

B

C

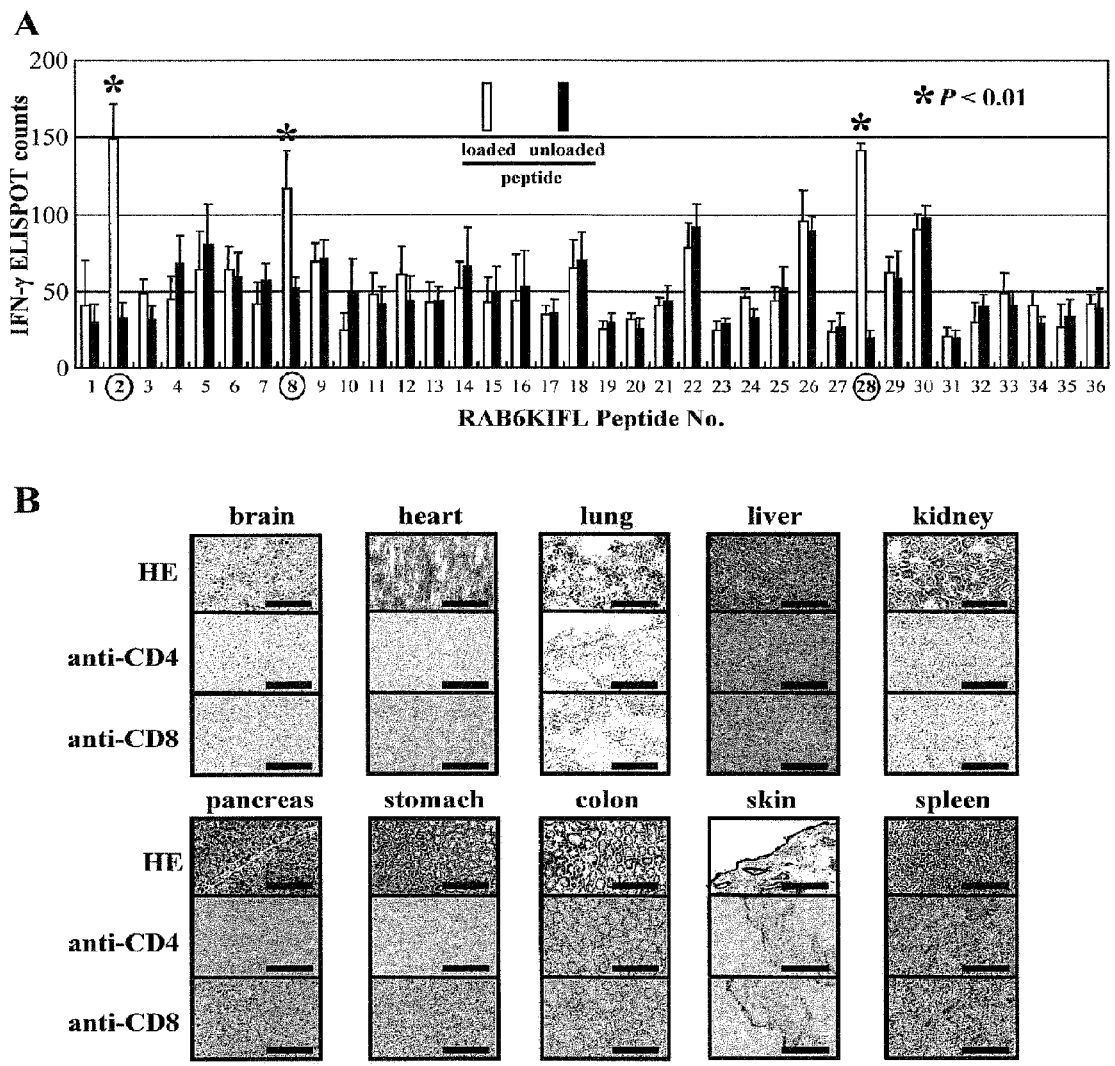

Fig. 6A-B
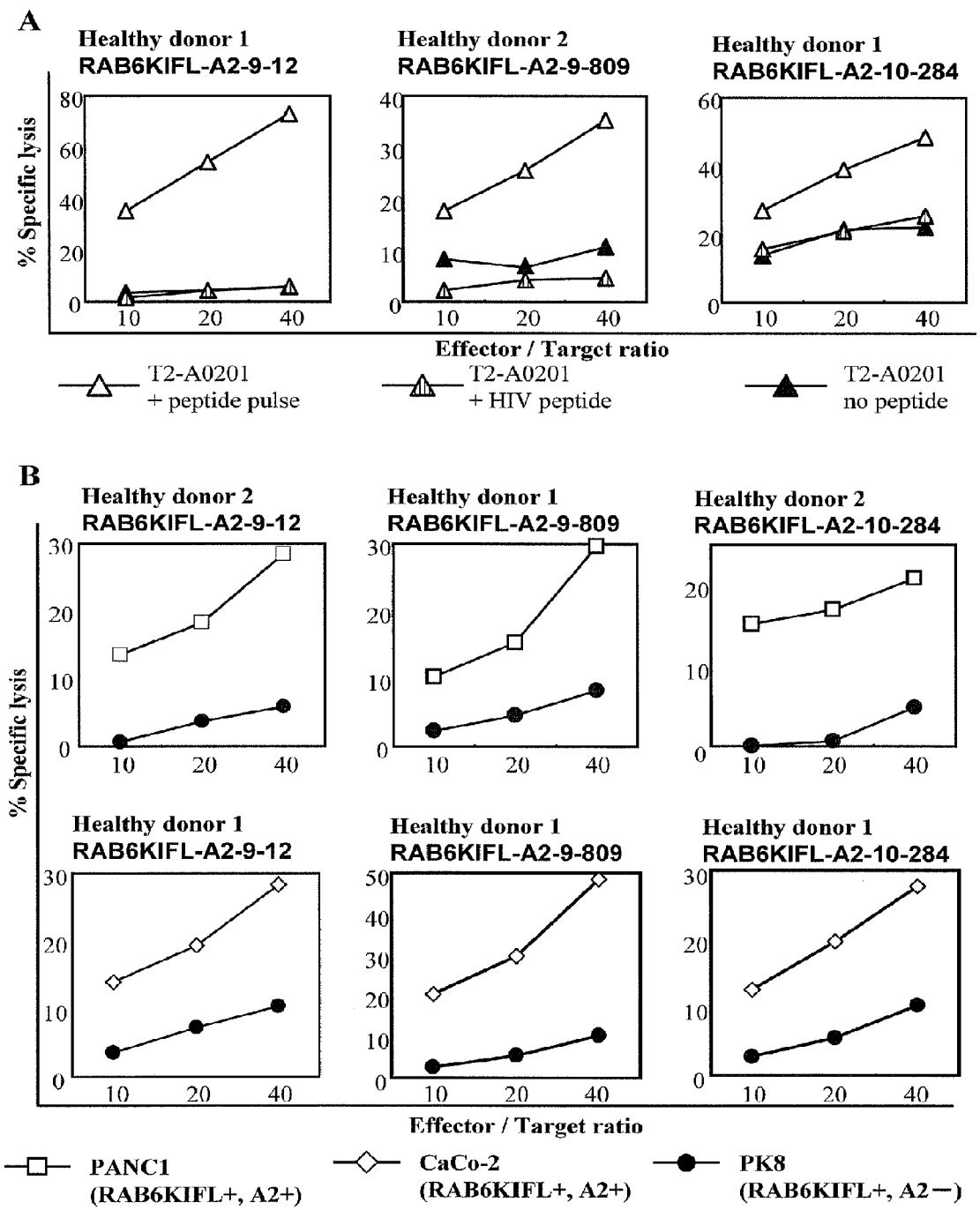

Fig. 6C-D
C
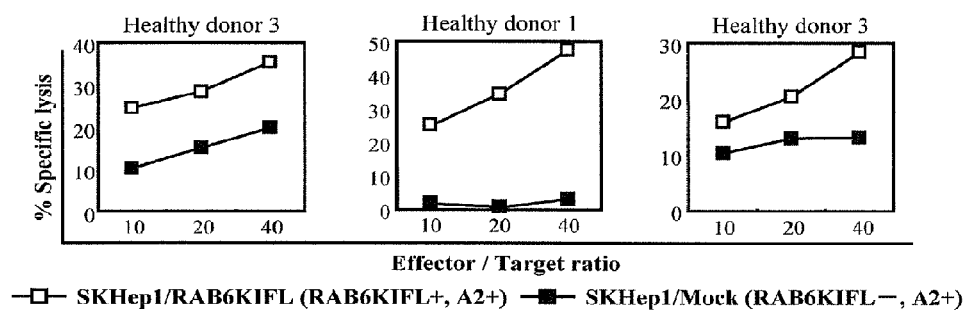
D
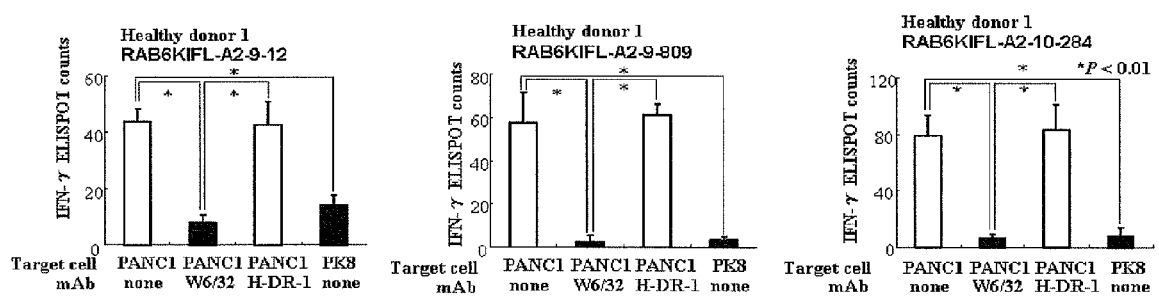

RAB6KIFL/KIF20A EPITOPE PEPTIDE AND VACCINES CONTAINING THE SAME

PRIORITY

The present application is a U.S. National Stage Application of PCT/JP2009/005382, filed Oct. 15, 2009, which claims the benefit of U.S. Provisional Application No. 61/197,106, filed on Oct. 22, 2008, the entire contents of which are incorporated by reference herein in their entirety.

TECHNICAL FIELD

The present invention relates to the field of biological science, more specifically to the field of cancer therapy. In particular, the present invention relates to novel oligopeptides and use thereof.

BACKGROUND ART

It has been demonstrated that CD8 positive CTLs recognize epitope peptides derived from the tumor-associated antigens (TAAs) found on major histocompatibility complex (MHC) class I molecule, and then kill the tumor cells. Since the discovery of the melanoma antigen (MAGE) family as the first example of TAAs, many other TAAs have been discovered, primarily through immunological approaches (NPL 1: Boon T, Int J Cancer 1993 May 8, 54(2): 177-80; NPL 2: Boon T & van der Bruggen P, J Exp Med 1996 Mar. 1, 183(3): 725-9). Some of the TAAs are now currently undergoing clinical development as immunotherapeutic targets.

Identification of new TAAs, capable of inducing potent and specific anti-tumor immune responses, warrants further development and clinical application of peptide vaccination strategies for various types of cancer (NPL 3: Harris C C, J Natl Cancer Inst 1996 Oct. 16, 88(20): 1442-55; NPL 4: Butterfield L H et al., Cancer Res 1999 Jul. 1, 59(13): 3134-42; NPL 5: Vissers J L et al., Cancer Res 1999 Nov. 1, 59(21): 5554-9; NPL 6: van der Burg S H et al., J Immunol 1996 May 1, 156(9): 3308-14; NPL 7: Tanaka F et al., Cancer Res 1997 Oct. 15, 57(20): 4465-8; NPL 8: Fujie T et al., Int J Cancer 1999 Jan. 18, 80(2): 169-72; NPL 9: Kikuchi M et al., Int J Cancer 1999 May 5, 81(3): 459-66; NPL 10: Oiso M et al., Int J Cancer 1999 May 5, 81(3): 387-94). To date, there have been several reports of clinical trials using these tumor-associated antigen derived peptides. Unfortunately, only a low objective response rate has been observed in these cancer vaccine trials so far (NPL 11: Belli F et al., J Clin Oncol 2002 Oct. 15, 20(20): 4169-80; NPL 12: Coulie P G et al., Immunol Rev 2002 October, 188: 33-42; NPL 13: Rosenberg S A et al., Nat Med 2004 September, 10(9): 909-15).

Recently, HLA class I-binding peptide sequence can be expected using algorithms (NPL 14: Journal of Immunological Methods, (1995), Vol. 185, pp. 181-190, NPL 15: J. Immunol., (1994), Vol. 152, pp. 163-175, NPL 16: protein science, (2000), Vol. 9, pp. 1838-1846). However, it is hard to say that the expected epitope peptide can be processed naturally in the target cells and expressed on the target cell surface with HLA molecule. Moreover, the algorithm, for example BIMAS (http://bimas.dcrt.nih.gov/cgi-bin/molbio/ken_parker_comboform) (NPL 17: Parker K C, et al., (1994) J. Immunol.; 152(1):163-75; NPL 18: Kuzushima K, et al., (2001) Blood; 98(6):1872-81.)) can suggest the HLA molecule-binding peptide, but the suggested peptide is not so rigorous (NPL 19: Bachinsky M M, et. al., Cancer Immun. 2005 Mar. 22; 5:6.). Thus TAA screening still remains a lot of challenges and difficulties.

Pancreatic cancer has a poor prognosis, with an overall 5-year survival rate of about 5% (1). A surgical resection remains the only option for a long term survival, but patients with resectable pancreatic cancer are in the minority (9-22%) (NPL 20: Sener S F, et al. J Am Coll Surg 1999; 189:1-7, NPL 21: Eloubeidi M A, et al. Am J Surg 2006; 192:322-9, NPL 22: Goonetilleke K S, et al. Int J Surg 2007; 5:147-51.). Even in these patients, however, the 5-year survival rate remains approximately 20% in spite of surgery with a curative intent (NPL 23: Smeenk H G, et al. Langenbecks Arch Surg 2005; 390:94-103, NPL 24: Yeo C J, et al. Ann Surg 1995; 221:721-31.). Up to 80% of patients present with locally advanced or metastatic disease, and their median survival ranges from 6 to 9 months (NPL 25: Lockhart A C, et al. Gastroenterology 2005; 128:1642-54.). Hence, the development of novel therapeutic modalities is an issue of great importance, and immunotherapy may be a potential treatment for pancreatic cancer.

RAB6KIFL (KIF20A) was first identified to play a role in the dynamics of the Golgi apparatus through direct interaction with Rab6 small GTPase (NPL 26: Echard A, et al. Science 1998; 279:580-5.). RAB6KIFL belongs to the kinesin superfamily of motor proteins, which have critical functions in trafficking of molecules and organelles (NPL 26: Echard A, et al. Science 1998; 279:580-5, NPL 27: Hirokawa N, et al. Curr Opin Cell Biol 1998; 10:60-73, NPL 28: Allan V J, and Schroer T A. Curr Opin Cell Biol 1999; 11:476-82.). Recently, Taniuchi K et al. reported that RAB6KIFL was overexpressed in pancreatic cancer tissues (NPL 29: Taniuchi K, et al. Cancer Res 2005; 65:105-12.). They found evidence for a critical role of RAB6KIFL in pancreatic carcinogenesis.

Through gene expression profile analysis using a genome-wide cDNA microarray containing 23,040 genes, RAB6KIFL (KIF20A) was recently shown to be up-regulated in several cancers such as bladder cancer (PTL 1: WO2006/085684), small cell lung cancer (SCLC) (PTL 2: WO2007/013665) and hormone-refractory prostate cancer (HRPC) (PTL 3: WO2008/102906), the disclosures of which are incorporated by reference herein. Further, some epitope peptides of KIF20A gene products were also identified (PTL 4: WO2008/102557).

CITATION LIST

Patent Literature

[PTL 1] WO2006/085684
[PTL 2] WO2007/013665
[PTL 3] WO2008/102906
[PTL 4] WO2008/102557

Non Patent Literature

[NPL 1] Boon T, Int J Cancer 1993 May 8, 54(2): 177-80
[NPL 2] Boon T & van der Bruggen P, J Exp Med 1996 Mar. 1, 183(3): 725-9
[NPL 3] Harris C C, J Natl Cancer Inst 1996 Oct. 16, 88(20): 1442-55
[NPL 4] Butterfield L H et al., Cancer Res 1999 Jul. 1, 59(13): 3134-42
[NPL 5] Vissers J L et al., Cancer Res 1999 Nov. 1, 59(21): 5554-9
[NPL 6] van der Burg S H et al., J Immunol 1996 May 1, 156(9): 3308-14
[NPL 7] Tanaka F et al., Cancer Res 1997 Oct. 15, 57(20): 4465-8
[NPL 8] Fujie T et al., Int J Cancer 1999 Jan. 18, 80(2): 169-72

[NPL 9] Kikuchi M et al., Int J Cancer 1999 May 5, 81(3): 459-66
[NPL 10] Oiso M et al., Int J Cancer 1999 May 5, 81(3): 387-94
[NPL 11] Belli F et al., J Clin Oncol 2002 Oct. 15, 20(20): 4169-80
[NPL 12] Coulie P G et al., Immunol Rev 2002 October, 188: 33-42
[NPL 13] Rosenberg S A et al., Nat Med 2004 September, 10(9): 909-15
[NPL 14] Journal of Immunological Methods, (1995), Vol. 185, pp. 181-190
[NPL 15] J. Immunol., (1994), Vol. 152, pp. 163-175
[NPL 16] protein science, (2000), Vol. 9, pp. 1838-1846
[NPL 17] Parker K C, et al., (1994) J. Immunol.; 152(1):163-75.
[NPL 18] Kuzushima K, et al., (2001) Blood; 98(6):1872-81.
[NPL 19] Bachinsky M M, et. al., Cancer Immun. 2005 Mar. 22; 5:6.
[NPL 20] Sener S F, et al. J Am Coll Surg 1999; 189:1-7.
[NPL 21] Eloubeidi M A, et al. Am J Surg 2006; 192:322-9.
[NPL 22] Goonetilleke K S, et al. Int J Surg 2007; 5:147-51.
[NPL 23] Smeenk H G, et al. Langenbecks Arch Surg 2005; 390:94-103.
[NPL 24] Yeo C J, et al. Ann Surg 1995; 221:721-31.
[NPL 25] Lockhart A C, et al. Gastroenterology 2005; 128: 1642-54.
[NPL 26] Echard A, et al. Science 1998; 279:580-5.
[NPL 27] Hirokawa N, et al. Curr Opin Cell Biol 1998; 10:60-73.
[NPL 28] Allan V J, and Schroer T A. Curr Opin Cell Biol 1999; 11:476-82.
[NPL 29] Taniuchi K, et al. Cancer Res 2005; 65:105-12.

SUMMARY OF INVENTION

The present invention is based in part on the discovery of new targets of immunotherapy. Because TAAs have often no immunogenicity, the discovery of appropriate targets is of extreme importance. In particular, the invention targets RAB6KIFL (SEQ ID NO: 2) encoded by the gene of GenBank Accession No. AF153329 or CR598555, also indicated by NM_005733 (SEQ ID NO: 1)), since RAB6KIFL has been identified as up-regulated in several cancers such as bladder cancer, breast cancer, cholangiocellular carcinoma, esophageal cancer, non-small cell lung cancer (NSCLC), pancreatic cancer, prostate cancer, renal carcinoma and small cell lung cancer (SCLC). The present invention provides RAB6KIFL gene products containing epitope peptides that elicit surprisingly strong CTL response that is specific to the corresponding molecules. Peripheral blood mononuclear cells (PBMCs) obtained from a healthy donor were stimulated using the peptides of the present invention. The present invention further provides established CTLs that specifically recognize HLA-A2 (A*0201) positive target cells pulsed with the respective peptides, and HLA-A2 (A*0201) restricted epitope peptides that can induce potent and specific immune responses against RAB6KIFL expressed on tumor. These results demonstrate that RAB6KIFL is strongly immunogenic and the epitopes thereof are effective targets for tumor immunotherapy.

Accordingly, it is an object of the present invention to provide oligopeptides having CTL inducibility as well as an amino acid sequence selected from the group of SEQ ID NOs: 3, 4 and 5. In addition, in another embodiment of the present invention, one, two or several amino acids may be substituted, deleted, inserted and/or added, so long as the resulting modified oligopeptides retain the CTL inducibility of the original peptides.

When administered to a subject, the present oligopeptides are presented on the surface of antigen-expressing cells and then induce CTLs targeting the respective peptides. Therefore, it is an object of the present invention to provide antigen-presenting cells and exosomes that present any of the present peptides, as well as methods for inducing antigen-presenting cells.

An anti-tumor immune response is induced by the administration of the present RAB6KIFL oligopeptides or polynucleotides encoding the oligopeptides, as well as exosomes and antigen-presenting cells which present the RAB6KIFL oligopeptides. Therefore, it is yet another object of the present invention to provide pharmaceutical agents or pharmaceutical composition containing the oligopeptides or polynucleotides encoding them, as well as the exosomes and antigen-presenting cells as their active ingredients. The pharmaceutical agents or pharmaceutical compositions of the present invention find use as vaccines.

Moreover, it is a further object of the present invention to provide methods for the treatment and/or prophylaxis of (i.e., prevention) cancers (tumors), and/or prevention of postoperative recurrence thereof, as well as methods for inducing CTLs, methods for inducing anti-tumor immunity, such methods including the step of administering the RAB6KIFL oligopeptides, polynucleotides encoding RAB6KIFL oligopeptides, exosomes or the antigen-presenting cells presenting RAB6KIFL polypeptides or the pharmaceutical agents of the present invention. In addition, the CTLs of the present invention also find use as vaccines against cancer. Examples of target cancers include, but are not limited to bladder cancer, breast cancer, cholangiocellular carcinoma, esophageal cancer, non-small cell lung cancer (NSCLC), pancreatic cancer, prostate cancer, renal carcinoma and small cell lung cancer (SCLC).

It is to be understood that both the foregoing summary of the present invention and the following detailed description are of exemplified embodiments, and not restrictive of the invention or other alternate embodiments of the invention.

BRIEF DESCRIPTION OF DRAWINGS

Various aspects and applications of the present invention will become apparent to the skilled artisan upon consideration of the brief description of the figures and the detailed description of the present invention and its preferred embodiments which follows:

FIG. 5 depicts identification of HLA-A2-restricted mouse CTL epitopes of human RAB6KIFL by using HLA-A2.1 (HHD) Tgm. A depicts the HLA-A2.1 (HHD) Tgm were immunized with $5\times10^5$ syngeneic BM-DCs pulsed with the twelve sets of the mixture of three kinds of peptides selected from 36 candidate peptides in vivo at day 7 and 14. On day 21, CD4-spleen cells isolated from immunized mice were stimulated with BM-DCs pulsed with each peptide for 6 days. The CTL-produced IFN-gamma was detected by an ELISPOT assay. RAB6KIFL-A2-9-12 (SEQ ID NO: 3), RAB6KIFL-A2-9-809 (SEQ TD NO: 4), and RAB6KIFL-A2-10-284 (SEQ TD NO: 5) peptides were shown to induce peptide-reactive CTLs. These assays were done twice with similar results. B depicts immunohistochemical staining with anti-CD4 or anti-CD8 mAb in tissue specimens of HLA-A2 (HHD) Tgm immunized with the RAB6KIFL-A2-9-809 peptide. After two-times vaccination, these specimens were resected and analyzed.

FIG. 6 depicts induction of RAB6KIFL-specific human CTL from the PBMCs of HLA-A2-positive healthy donors. A depicts that the RAB6KIFL peptide-reactive CTLs were generated from the PBMCs of HLA-A2-positive healthy donors. After three stimulations with autologous monocyte-derived DCs pulsed with the RAB6KIFL-A2-9-12 (SEQ ID NO: 3), RAB6KIFL-A2-9-809 (SEQ ID NO:4), and RAB6KIFL-A2-10-284 (SEQ ID NO:5) peptide, the cytotoxicity of the CTLs against T2 cells (HLA-A2+, TAP deficient), pulsed with each peptide or peptide-unpulsed T2 cells, was detected by standard a $^{51}$Cr release assay. These CTLs exhibited cytotoxicity to the RAB6KIFL-A2-9-12 (left), RAB6KIFL-A2-9-809 (middle), and RAB6KIFL-A2-10-284 (right) peptide pulsed T2 cells, but not to irrelevant HIV peptide and peptide-unpulsed T2 cells. B depicts that these CTLs exhibited cytotoxicity to the RAB6KIFL+HLA-A2 (A*0201)$^+$ human pancreatic cancer cell line PANC1 and colon cancer cell line CaCo-2, but not to RAB6KIFL+HLA-A2 (A*0201)$^-$ human pancreatic cancer cell line PK8.

Figure 1:
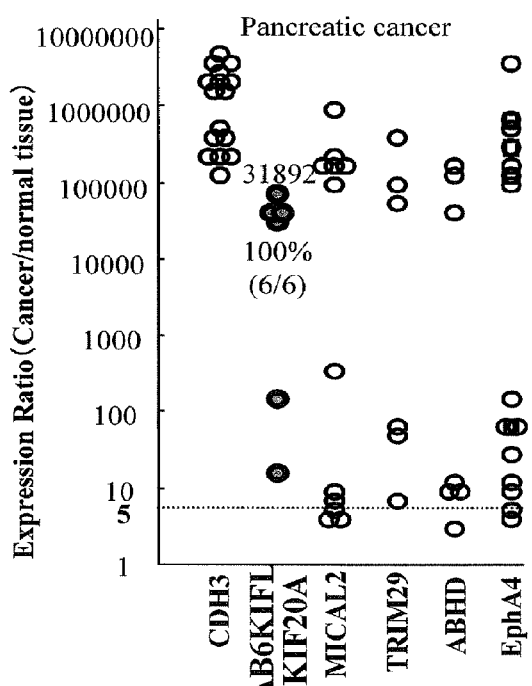
FIG. 1 depicts markedly and frequently enhanced expression of RAB6KIFL mRNA in pancreatic cancer tissues as based on a cDNA microarray analysis. A depicts a list of up-regulated genes in pancreatic cancer cells. These genes were overexpressed in cancer cells in comparison to their normal counterparts. The expression of RAB6KIFL mRNA in pancreatic cancer cells was markedly enhanced in all of 6 pancreatic cancer patients. B depicts the relative expression ratio of RAB6KIFL gene in normal tissues based on a cDNA microarray analysis. RAB6KIFL gene was faintly expressed only in the testis and thymus. C depicts the expression level of the RAB6KIFL gene was also enhanced in many lung and bladder cancers as well as pancreatic cancer based on the previous cDNA microarray analysis.
Figure 1:
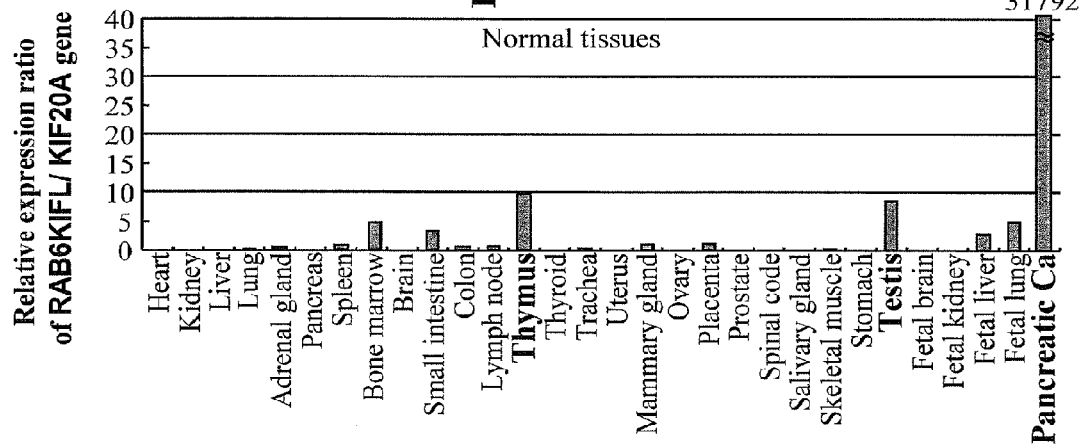

C depicts the cytotoxicity of these CTLs was RAB6KIFL-specific. These CTLs killed SKHep1/RAB6KIFL, a RAB6KIFL$^{low}$ HLA-A2+ human liver cancer cell line SKHep1 transfected with human RAB6KIFL gene, but not killed SKHep1/Mock. D depicts the inhibition of cytotoxicity by anti-HLA-class I mAb. After the target cells PANC1 were incubated with anti-HLA-class I mAb (W6/32, IgG$_{2a}$) or anti-HLA-DR mAb (H-DR-1, IgG$_{2a}$) respectively for 1 hour, the CTLs generated from the PBMCs of healthy donor by stimulation with RAB6KIFL-A2-9-12 (upper), RAB6KIFL-A2-9-809 (middle), and RAB6KIFL-A2-10-284 (lower) peptide were added. IFN-gamma productions were markedly inhibited by W6/32, but not by H-DR-1.

DESCRIPTION OF EMBODIMENTS

Although any methods and materials similar or equivalent to those described herein can be used in the practice or testing of embodiments of the present invention, the preferred methods, devices, and materials are now described. However, before the present materials and methods are described, it is to be understood that the present invention is not limited to the particular sizes, shapes, dimensions, materials, methodologies, protocols, etc. described herein, as these may vary in accordance with routine experimentation and optimization. It is also to be understood that the terminology used in the description is for the purpose of describing the particular versions or embodiments only, and is not intended to limit the scope of the present invention which will be limited only by the appended claims.

The disclosure of each publication, patent or patent application mentioned in this specification is specifically incorporated by reference herein in its entirety. However, nothing herein is to be construed as an admission that the invention is not entitled to antedate such disclosure by virtue of prior invention.

In case of conflict, the present specification, including definitions, will control. In addition, the materials, methods, and examples are illustrative only and not intended to be limiting.

I. DEFINITIONS

The words "a", "an", and "the" as used herein mean "at least one" unless otherwise specifically indicated.

The terms "polypeptide", "peptide" and "protein" are used interchangeably herein to refer to a polymer of amino acid residues. The terms apply to amino acid polymers in which one or more amino acid residue is a modified residue, or a non-naturally occurring residue, such as an artificial chemical mimetic of a corresponding naturally occurring amino acid, as well as to naturally occurring amino acid polymers.

The term "oligopeptide" sometimes used in the present specification is used to refer to peptides of the present invention which are 20 residues or fewer, typically 15 residues or fewer in length and usually consist of between about 8 and about 11 residues, often 9 or 10 residues.

The term "amino acid" as used herein refers to naturally occurring and synthetic amino acids, as well as amino acid analogs and amino acid mimetics that similarly function to the naturally occurring amino acids. Naturally occurring amino acids are those encoded by the genetic code, as well as those modified after translation in cells (e.g., hydroxyproline, gamma-carboxyglutamate, and O-phosphoserine). The phrase "amino acid analog" refers to compounds that have the same basic chemical structure (an alpha carbon bound to a hydrogen, a carboxy group, an amino group, and an R group) as a naturally occurring amino acid but have a modified R group or modified backbones (e.g., homoserine, norleucine, methionine, sulfoxide, methionine methyl sulfonium). The phrase "amino acid mimetic" refers to chemical compounds that have different structures but similar functions to general amino acids.

Amino acids may be referred to herein by their commonly known three letter symbols or the one-letter symbols recommended by the IUPAC-IUB Biochemical Nomenclature Commission.

The terms "gene", "polynucleotides", "nucleotides" and "nucleic acids" are used interchangeably herein unless otherwise specifically indicated and are similarly to the amino acids referred to by their commonly accepted single-letter codes.

Unless otherwise defined, the terms "cancer" refers to cancers over-expressing the RAB6KIFL gene. Examples of cancers over-expressing RAB6KIFL include, but are not limited to, bladder cancer, breast cancer, cholangiocellular carcinoma, esophageal cancer, non-small cell lung cancer (NSCLC), pancreatic cancer, prostate cancer, renal carcinoma and small cell lung cancer (SCLC).

Unless otherwise defined, the term "cytotoxic T lymphocyte", "cytotoxic T cell" and "CTL" are used interchangeably herein and, unless otherwise specifically indicated, refer to a sub-group of T lymphocytes that are capable of recognizing non-self cells (e.g., tumor cells, virus-infected cells) and inducing the death of such cells.

Unless otherwise defined, all technical and scientific terms used herein have the same meaning as commonly understood by one of ordinary skill in the art to which this invention belongs.

II. PEPTIDES

To demonstrate that peptides derived from RAB6KIFL function as an antigen recognized by cytotoxic T lymphocytes (CTLs), peptides derived from RAB6KIFL (SEQ ID NO: 2) were analyzed to determine whether they were antigen epitopes restricted by HLA-A2 (A*0201) which are commonly encountered HLA alleles (Date Y et al., Tissue Antigens 47: 93-101, 1996; Kondo A et al., J Immunol 155: 4307-12, 1995; Kubo R T et al., J Immunol 152: 3913-24, 1994). Candidates of HLA-A2 binding peptides derived from RAB6KIFL were identified using the information on their binding affinities to HLA-A2. After in vitro stimulation of T-cells by dendritic cells (DCs) loaded with these peptides, CTLs were successfully established using each of the peptides, particularly following peptides:

```
RAB6KIFL-A2-9-12,    (SEQ ID NO: 3)

RAB6KIFL-A2-9-809,   (SEQ ID NO: 4)
and

RAB6KIFL-A2-10-284.  (SEQ ID NO: 5)
```

These established CTLs show potent specific CTL activity against target cells pulsed with respective peptides. The results herein demonstrate that RAB6KIFL is an antigen recognized by CTL and that the peptides may be epitope peptides of RAB6KIFL restricted by HLA-A2 (A*0201).

Since the RAB6KIFL gene is over expressed in most cancer tissues, such as bladder cancer, breast cancer, cholangiocellular carcinoma, esophageal cancer, non-small cell lung cancer (NSCLC), pancreatic cancer, prostate cancer, renal carcinoma and small cell lung cancer (SCLC), it is a good target for immunotherapy. Thus, the present invention provides oligopeptides such as nonapeptides (peptides consisting of nine amino acid residues) and decapeptides (peptides consisting of ten amino acid residues) corresponding to CTL-recognized epitopes of RAB6KIFL. Particularly preferred examples of oligopeptides of the present invention include those peptides having an amino acid sequence selected from among SEQ ID NOs: 3, 4 and 5.

Generally, software programs now available on the Internet, such as those described in Parker K C et al., J Immunol 1994 Jan. 1, 152(1): 163-75, can be used to calculate the binding affinities between various peptides and HLA antigens in silico. Binding affinity with HLA antigens can be measured as described, for example, in Parker K C et al., J Immunol 1994 Jan. 1, 152(1): 163-75; and Kuzushima K et al., Blood 2001, 98(6): 1872-81. The methods for determining binding affinity is described, for example, in; Journal of Immunological Methods, 1995, 185: 181-190; Protein Science, 2000, 9: 1838-1846. Thus, the present invention encompasses peptides of RAB6KIFL which are determined to bind with HLA antigens by such known programs.

Furthermore, these peptides of the present invention can be flanked with additional amino acid residues so long as the peptide retains its CTL inducibility. Such peptides with CTL inducibility are, for example, less than about 40 amino acids, often less than about 20 amino acids, usually less than about 15 amino acids. The amino acid sequence flanking the peptides consisting of the amino acid sequence selected from the group of SEQ ID NOs: 3, 4 and 5 is not limited and can be composed of any kind of amino acids so long as it does not impair the CTL inducibility of the original peptide. Thus, the present invention also provides peptides having CTL inducibility, which comprises the amino acid sequence selected from the group of SEQ TD NOs: 3, 4 and 5.

In general, modification of one, two, or several amino acids in a protein will not influence the function of the protein, or in some cases even enhance the desired function of the original protein. In fact, modified peptides (i.e., peptides composed of an amino acid sequence in which one, two or several amino acid residues have been modified (i.e., substituted, deleted, added and/or inserted) as compared to an original reference sequence) have been known to retain the biological activity of the original peptide (Mark et al., Proc Natl Acad Sci USA 1984, 81: 5662-6; Zoller and Smith, Nucleic Acids Res 1982, 10: 6487-500; Dalbadie-McFarland et al., Proc Natl Acad Sci USA 1982, 79: 6409-13). Thus, in one embodiment, the oligopeptides of the present invention may have both CTL inducibility and an amino acid sequence selected from the group of SEQ ID NOs: 3, 4 and 5 wherein one, two or several amino acids are added, inserted, deleted, and/or substituted.

Those of skill in the art recognize that individual additions or substitutions to an amino acid sequence which alters a single amino acid or a small percentage of amino acids tend to result in the conservation of the properties of the original amino acid side-chain. As such, they are conventionally referred to as "conservative substitutions" or "conservative modifications", wherein the alteration of a protein results in a modified protein having properties and functions analogous to the original protein. Conservative substitution tables providing functionally similar amino acids are well known in the art. Examples amino acid side chain characteristics that are desirable to conserve include, for example, hydrophobic amino acids (A, I, L, M, F, P, W, Y, V), hydrophilic amino acids (R, D, N, C, E, Q, G, H, K, S, T), and side chains having the following functional groups or characteristics in common: an aliphatic side-chain (G, A, V, L, I, P); a hydroxyl group containing side-chain (S, T, Y); a sulfur atom containing side-chain (C, M); a carboxylic acid and amide containing side-chain (D, N, E, Q); a base containing side-chain (R, K, H); and an aromatic containing side-chain (H, F, Y, W). In addition, the following eight groups each contain amino acids that are accepted in the art as conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M) (see, e.g., Creighton, Proteins 1984).

Such conservatively modified peptides are also considered to be peptides of the present invention. However, peptides of the present invention are not restricted thereto and can include non-conservative modifications, so long as the peptide retains the CTL inducibility of the original peptide. Furthermore, modified peptides should not exclude CTL inducible peptides of polymorphic variants, interspecies homologues, and alleles of RAB6KIFL.

To retain the requisite CTL inducibility one can modify (add or substitute) a small number (for example, 1, 2 or several) or a small percentage of amino acids. Herein, the term "several" means 5 or fewer amino acids, for example, 3 or fewer. The percentage of amino acids to be modified can be 20% or less, for example, 15% of less, for example 10% or 1 to 5%.

When used in the context of immunotherapy, peptides of the present invention should be presented on the surface of a cell or exosome, preferably as a complex with an HLA antigen. Therefore, t is preferable to select peptides that not only induce CTLs but also that possess high binding affinity to the HLA antigen. To that end, the peptides can be modified by substitution, insertion, deletion, and/or addition of the amino acid residues to yield a modified peptide having improved binding affinity. In addition to peptides that are naturally displayed, since the regularity of the sequences of peptides displayed by binding to HLA antigens is already known (J Immunol 1994, 152: 3913; Immunogenetics 1995, 41: 178; J Immunol 1994, 155: 4307), modifications based on such regularity can be introduced into the immunogenic peptides of the invention. For example, peptides possessing high HLA-A2 (A*0201) binding affinity have their second amino acid from the N-terminus substituted with leucine or methionine, and peptides whose amino acid at C-terminus is substituted with valine or leucine. Thus, peptides having the amino acid sequences of SEQ ID NOs: 3, 4 or 5 wherein the second amino acid from the N-terminus is substituted with leucine or methionine and/or wherein the C-terminus is substituted with valine or leucine, are encompassed by the present invention. Substitutions can be introduced not only at the terminal amino acids but also at the position of potential TCR recognition of peptides. Several studies have demonstrated that amino acid substitutions in a peptide can be equal to or better than the original, for example CAP1, p53$_{(264-272)}$, Her-2/neu$_{(369-377)}$ or gp100$_{(209-217)}$ (Zaremba et al. Cancer Res. 57, 4570-4577, 1997, T. K. Hoffmann et al. J. Immunol. (2002) Feb. 1; 168(3):1338-47, S. O. Dionne et al. Cancer Immunol immunother. (2003) 52: 199-206 and S. O. Dionne et al. Cancer Immunology, Immunotherapy (2004) 53, 307-314).

The present invention also contemplates the addition of amino acids to the sequences disclosed here. For example, one, two or several amino acids can also be added to the N and/or C-terminus of the present peptides. Such modified peptides having high HLA antigen binding affinity and retained CTL inducibility are also included in the present invention.

However, when the peptide sequence is identical to a portion of the amino acid sequence of an endogenous or exogenous protein having a different function, side effects such as autoimmune disorders and/or allergic symptoms against specific substances may be induced. Therefore, it is preferable to first perform homology searches using available databases to avoid situations in which the sequence of the peptide matches the amino acid sequence of another protein. When it becomes clear from the homology searches that no peptide exists with as few as 1 or 2 amino acid differences as compared to the objective peptide, the objective peptide can be modified in order to increase its binding affinity with HLA antigens, and/or increase its CTL inducibility without any danger of such side effects.

Although peptides having high binding affinity to the HLA antigens as described above are expected to be highly effective, the candidate peptides, which are selected according to the presence of high binding affinity as an indicator, are further examined for the presence of CTL inducibility. Herein, the phrase "CTL inducibility" indicates the ability of the peptide to induce cytotoxic lymphocytes (CTLs) when presented on antigen-presenting cells. Further, "CTL inducibility" includes the ability of the peptide to induce CTL activation, CTL proliferation, promote CTL lysis of target cells, and to increase CTL IFN-gamma production.

Confirmation of CTL inducibility is accomplished by inducing antigen-presenting cells carrying human MHC antigens (for example, B-lymphocytes, macrophages, and dendritic cells (DCs)), or more specifically DCs derived from human peripheral blood mononuclear leukocytes, and after stimulation with the peptides, mixing with CD8-positive cells, and then measuring the IFN-gamma produced and released by CTL against the target cells. As the reaction system, transgenic animals that have been produced to express a human HLA antigen (for example, those described in BenMohamed L, Krishnan R, Longmate J, Auge C, Low L, Primus J, Diamond D J, Hum Immunol 2000 August, 61(8): 764-79, Related Articles, Books, Linkout Induction of CTL response by a minimal epitope vaccine in HLA A*0201/DR1 transgenic mice: dependence on HLA class II restricted T(H) response) can be used. For example, the target cells can be radio-labeled with $^{51}$Cr and such, and cytotoxic activity can be calculated from radioactivity released from the target cells. Alternatively, CTL inducibility can be assessed by measuring IFN-gamma produced and released by CTL in the presence of antigen-presenting cells (APCs) that carry immobilized peptides, and visualizing the inhibition zone on the media using anti-IFN-gamma monoclonal antibodies.

As a result of examining the CTL inducibility of the peptides as described above, it was discovered that those peptides having high binding affinity to an HLA antigen did not necessarily have high CTL inducibility. However, of those peptides identified and assessed, nonapeptides or decapeptides selected from peptides having an amino acid sequences indicated by SEQ ID NOs: 3, 4 and 5, were found to exhibit particularly high CTL inducibility as well as high binding affinity to an HLA antigen. Thus, these peptides are exemplified as preferred embodiments of the present invention.

In addition to the above-described modifications, the peptides of the present invention can also be linked to other substances, so long as the resulting linked peptide retains the requisite CTL inducibility of the original peptide. Examples of suitable substances include, but are not limited to: peptides, lipids, sugar and sugar chains, acetyl groups, natural and synthetic polymers, etc. The peptides can contain modifications such as glycosylation, side chain oxidation, or phosphorylation, etc. provided the modifications do not destroy the biological activity of the original peptide. These kinds of modifications can be performed to confer additional functions (e.g., targeting function, and delivery function) or to stabilize the polypeptide.

For example, to increase the in vivo stability of a polypeptide, it is known in the art to introduce D-amino acids, amino acid mimetics or unnatural amino acids; this concept can also be adapted to the present polypeptides. The stability of a polypeptide can be assayed in a number of ways. For instance, peptidases and various biological media, such as human plasma and serum, can be used to test stability (see, e.g., Verhoef et al., Eur J Drug Metab Pharmacokin 1986, 11: 291-302).

Further, the peptides of the present invention may be linked to other peptides via spacers or linkers. Examples of other peptides include, but are not limited to, CTL inducible peptides derived from other TAAs. Alternatively, two or more peptides of the present invention may be linked via spacers or linkers. The peptides linked via spacers or linkers may be the same or different each other. Spacers or linkers are not specifically limited, but are preferably peptides, more preferably peptides having one or more cleavage sites which are capable of being cleaved by enzymes such as peptidases, proteases and proteasomes. Examples of linkers or spacers include, but are not limited to: AAY (P. M. Daftarian et al., J Trans Med 2007, 5:26), AAA, NKRK (R. P. M. Sutmuller et al., J. Immunol. 2000, 165: 7308-7315) or, one to several lysine residues (S. Ota et al., Can Res. 62, 1471-1476, K. S. Kawamura et al., J. Immunol. 2002, 168: 5709-5715). The peptides of the present invention encompass those peptides linked to other peptides via spacers or linkers.

Herein, the peptides of the present invention can also be described as "RAB6KIFL peptide(s)", "RAB6KIFL polypeptide(s)" or "RAB6KIFL oligopeptide".

III. PREPARATION OF RAB6KIFL PEPTIDES

The peptides of the present invention can be prepared using well known techniques. For example, the peptides can be prepared synthetically, using recombinant DNA technology or chemical synthesis. The peptides of the present invention can be synthesized individually or as longer polypeptides composed of two or more peptides. The peptides can then be isolated i.e., purified or isolated so as to be substantially free of other naturally occurring host cell proteins and fragments thereof, or any other chemical substances.

A peptide of the present invention can be obtained through chemical synthesis based on the selected amino acid sequence. Examples of conventional peptide synthesis methods that can be adapted to the synthesis include, but are not limited to:

(i) Peptide Synthesis, Interscience, New York, 1966;
(ii) The Proteins, Vol. 2, Academic Press, New York, 1976;
(iii) Peptide Synthesis (in Japanese), Maruzen Co., 1975;
(iv) Basics and Experiment of Peptide Synthesis (in Japanese), Maruzen Co., 1985;
(v) Development of Pharmaceuticals (second volume) (in Japanese), Vol. 14 (peptide synthesis), Hirokawa, 1991;
(vi) WO99/67288; and
(vii) Barany G. & Merrifield R. B., Peptides Vol. 2, "Solid Phase Peptide Synthesis", Academic Press, New York, 1980, 100-118.

Alternatively, the present peptides can be obtained adapting any known genetic engineering methods for producing peptides (e.g., Morrison J, J Bacteriology 1977, 132: 349-51; Clark-Curtiss & Curtiss, Methods in Enzymology (eds. Wu et al.) 1983, 101: 347-62). For example, first, a suitable vector harboring a polynucleotide encoding the objective peptide in an expressible form (e.g., downstream of a regulatory sequence corresponding to a promoter sequence) is prepared and transformed into a suitable host cell. The host cell is then cultured to produce the peptide of interest. The peptide can also be produced in vitro adopting an in vitro translation system.

IV. POLYNUCLEOTIDES

The present invention also provides a polynucleotide which encodes any of the aforementioned peptides of the present invention. These include polynucleotides derived from the natural occurring RAB6KIFL/KIF20A gene (GenBank Accession No. NM_005733 (SEQ ID NO: 1)) as well as those having a conservatively modified nucleotide sequence thereof. Herein, the phrase "conservatively modified nucleotide sequence" refers to sequences which encode identical or essentially identical amino acid sequences. Due to the degeneracy of the genetic code, a large number of functionally identical nucleic acids encode any given protein. For instance, the codons GCA, GCC, GCG, and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a peptide also describes every possible silent variation of the nucleic acid. One of ordinary skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a peptide is implicitly described in each disclosed sequence.

The polynucleotide of the present invention can be composed of DNA, RNA, and derivatives thereof. A DNA is suitably composed of bases such as A, T, C, and G, and T is replaced by U in an RNA.

The polynucleotide of the present invention can encode multiple peptides of the present invention with or without intervening amino acid sequences in between. For example, the intervening amino acid sequence can provide a cleavage site (e.g., enzyme recognition sequence) of the polynucleotide or the translated peptides. Furthermore, the polynucleotide can include any additional sequences to the coding sequence encoding the peptide of the present invention. For example, the polynucleotide can be a recombinant polynucleotide that includes regulatory sequences required for the expression of the peptide or can be an expression vector (plasmid) with marker genes and such. In general, such recombinant polynucleotides can be prepared by the manipulation of polynucleotides through conventional recombinant techniques using, for example, polymerases and endonucleases.

Both recombinant and chemical synthesis techniques can be used to produce the polynucleotides of the present invention. For example, a polynucleotide can be produced by insertion into an appropriate vector, which can be expressed when transfected into a competent cell. Alternatively, a polynucleotide can be amplified using PCR techniques or expression in suitable hosts (see, e.g., Sambrook et al., Molecular Cloning: A Laboratory Manual, Cold Spring Harbor Laboratory, New York, 1989). Alternatively, a polynucleotide can be synthesized using the solid phase techniques, as described in Beaucage S L & Iyer R P, Tetrahedron 1992, 48: 2223-311; Matthes et al., EMBO J 1984, 3: 801-5.

Vectors containing the polynucleotide of the present invention and host cells harboring the vectors are also included in the present invention.

V. EXOSOMES

The present invention further provides intracellular vesicles called exosomes, which present complexes formed between the peptides of this invention and HLA antigens on their surface. Exosomes can be prepared, for example by using the methods detailed in Japanese Patent Application Kohyo Publications Nos. Hei 11-510507 and WO99/03499, and can be prepared using APCs obtained from patients who are subject to treatment and/or prevention. The exosomes of this invention can be inoculated as vaccines, in a fashion similar to the peptides of this invention.

The type of HLA antigens comprised in the complexes must match that of the subject requiring treatment and/or prevention. The use of HLA-A2 type that is highly expressed among the Japanese and Caucasian is favorable for obtaining effective results, and subtypes such as HLA-A2 (A*0201) and HLA-A2 (A*0206) find use. Typically, in the clinic, the type of HLA antigen of the patient requiring treatment is investigated in advance, which enables appropriate selection of peptides having high levels of binding affinity to this antigen, or having CTL inducibility by antigen presentation. Furthermore, in order to obtain peptides showing high binding affinity and CTL inducibility, substitution or addition of 1, 2, or several amino acids can be performed based on the amino acid sequence of the naturally occurring RAB6KIFL partial peptide.

When using HLA-A2 (A*0201) antigen for the exosome of the present invention, a peptide having the sequence selected peptide of SEQ ID NO: 3, 4 and 5 finds use.

VI. ANTIGEN-PRESENTING CELLS (APCS)

The present invention also provides isolated APCs that present complexes formed between HLA antigens and the peptides of this invention on its surface. The APCs that are obtained by contacting the peptides of this invention, or introducing the polynucleotides encoding the peptides of this invention in an expressible form can be derived from patients who are subject to treatment and/or prevention, and can be administered as vaccines by themselves or in combination with other drugs including the peptides of this invention, exosomes, or cytotoxic T cells.

The APCs are not limited to a particular kind of cells and include dendritic cells (DCs), Langerhans cells, macrophages, B cells, and activated T cells, which are known to present proteinaceous antigens on their cell surface so as to be recognized by lymphocytes. Since DC is a representative APC having the strongest CTL inducing action among APCs, DCs find use as the APCs of the present invention.

For example, an APC can be obtained by inducing DCs from peripheral blood monocytes and then contacting (stimulating) them with the peptides of this invention in vitro, ex vivo or in vivo. When the peptides of this invention are administered to the subjects, APCs that present the peptides of this invention are induced in the body of the subject. The phrase "inducing APC" includes contacting (stimulating) a cell with the peptides of this invention, or nucleotides encoding the peptides of this invention to present complexes formed between HLA antigens and the peptides of this invention on cell's surface. Alternatively, after introducing the peptides of this invention to the APCs to allow the APCs to present the peptides, the APCs can be administered to the subject as a vaccine. For example, the ex vivo administration can include the steps of:

a: collecting APCs from a first subject:
b: contacting with the APCs of step a, with the peptide; and
c: administering the peptide-loaded APCs to a second subject.

The first subject and the second subject can be the same individual, or may be different individuals. Alternatively, according to the present invention, use of the peptides of this invention for manufacturing a pharmaceutical composition inducing antigen-presenting cells is provided. In addition, the present invention provides a method or process for manufacturing a pharmaceutical composition for inducing antigen-presenting cells, wherein the method includes the step of admixing or formulating the peptide of the present invention with a pharmaceutically acceptable carrier. Alternatively, the present invention provides a method or process for manufacturing a pharmaceutical composition for treating cancers including bladder cancer, breast cancer, cholangiocellular carcinoma, esophageal cancer, non-small cell lung cancer (NSCLC), pancreatic cancer, prostate cancer, renal carcinoma and small cell lung cancer (SCLC), wherein the method includes the step of admixing or formulating the peptide of the present invention with a pharmaceutically acceptable carrier. Further, the present invention also provides the peptides of the present invention for inducing antigen-presenting cells. The APCs obtained by step b can be administered to the subject as a vaccine. Alternatively, the present invention provides the peptides for treating cancers including bladder cancer, breast cancer, cholangiocellular carcinoma, esophageal cancer, non-small cell lung cancer (NSCLC), pancreatic cancer, prostate cancer, renal carcinoma and small cell lung cancer (SCLC).

According to an aspect of the present invention, the APCs of the present invention have a high level of CTL inducibility. In the term of "high level of CTL inducibility", the high level is relative to the level of that by APC contacting with no peptide or peptides which can not induce the CTL. Such APCs having a high level of CTL inducibility can be prepared by a method which includes the step of transferring genes containing polynucleotides that encode the peptides of this invention to APCs in vitro. The introduced genes can be in the form of DNAs or RNAs. Examples of methods for introduction include, without particular limitations, various methods conventionally performed in this field, such as lipofection, electroporation, and calcium phosphate method can be used. More specifically, it can be performed as described in Cancer Res 1996, 56: 5672-7; J Immunol 1998, 161: 5607-13; J Exp Med 1996, 184: 465-72; Published Japanese Translation of International Publication No. 2000-509281. By transferring the gene into APCs, the gene undergoes transcription, translation, and such in the cell, and then the obtained protein is processed by MHC Class I or Class II, and proceeds through a presentation pathway to present peptides.

In a preferred embodiment, the APCs of the present invention present on its surface a complex of an HLA antigen and a oligopeptide comprising an amino acid sequence selected from among SEQ ID NO: 3, 4 and 5. Preferably, the APCs of the present invention carry HLA-A2 antigen, in particular HLA-A2 (A*0201) on its surface. Alternatively, oligopeptide to form complex with an HLA antigen may be a oligopeptide comprising an amino acid sequence selected from among SEQ ID NO: 3, 4, and 5, wherein one, two or several amino acids are substituted, inserted, deleted and/or added, for example, the second amino acid from the N-terminus may be substituted with leucine or methionine, and/or the C-terminal amino acid may be substituted with valine or leucine.

VII. CYTOTOXIC T CELLS (CTLS)

A cytotoxic T cell induced against any of the peptides of the present invention strengthens the immune response targeting tumor-associated endothelia in vivo and thus can be used as vaccines, in a fashion similar to the peptides per se. Thus, the present invention also provides isolated cytotoxic T cells that are specifically induced or activated by any of the present peptides.

Such cytotoxic T cells can be obtained by (1) administering to a subject, and then collecting cytotoxic T cells from the subject, or (2) contacting (stimulating) subject-derived APCs, and CD8-positive cells, or peripheral blood mononuclear leukocytes in vitro with the peptides of the present invention and then isolating cytotoxic T cells.

The cytotoxic T cells, which have been induced by stimulation from APCs that present the peptides of this invention, can be derived from patients who are subject to treatment and/or prevention, and can be administered by themselves or in combination with other drugs including the peptides of this invention or exosomes for the purpose of regulating effects. The obtained cytotoxic T cells act specifically against target cells presenting the peptides of this invention, or for example, the same peptides used for induction. In the other word, the cytotoxic T cells can recognize (i.e., binding to) a complex formed between a HLA antigen and the peptide of the present invention on a target cell surface with the T cell receptor, and then attack the target cell to induce the death of the target cell. The target cells can be cells that endogenously express RAB6KIFL, or cells that are transfected with the RAB6KIFL gene; and cells that present a peptide of this invention on the cell surface due to stimulation by the peptide can also serve as targets of activated CTL attack. In the preferred embodiment, the target cells carry HLA-A2 antigen, in particular HLA-A2 (A*020) on its surface.

VIII. T CELL RECEPTOR (TCR)

The present invention also provides a composition composed of a nucleic acid sequence encoding polypeptides that are capable of forming a subunit of a T cell receptor (TCR), and methods of using the same. The TCR alpha and beta have the ability to form TCR that confer specificity to T cells against tumor cells expressing RAB6KIFL. By using the known methods in the art, the nucleic acid sequence of TCR alpha and beta chains of the TCR expressed in the CTL induced with one or more peptides of this invention can be isolated and used to construct suitable vectors that can mediate high efficiency gene transfer into primary human lymphocytes (WO2007/032255 and Morgan R A, et al., J Immunol, 171, 3287 (2003)). For example, these vectors are retroviral vectors. Advantageously, the invention provides an off-the-shelf composition allowing rapid modification of a patient's own T cells (or those of another mammal) to rapidly and easily produce modified T cells having excellent cancer cell killing properties.

Also, the present invention provides CTLs which are prepared by transduction with the nucleic acids encoding the TCR subunits polypeptides that bind to the RAB6KIFL peptide e.g. SEQ ID NOs: 3, 4 and 5 in the context of HLA-A2 (A*0201). The transduced CTLs are capable of homing to cancer cells in vivo, and can be expanded by well known culturing methods in vitro (e.g., Kawakami et al., J Immunol., 142, 3452-3461 (1989)). The T cells of the invention can be used to form an immunogenic composition useful in treating or the prevention of cancer in a patient in need of therapy or protection (WO2006/031221).

IX. PHARMACEUTICAL AGENTS OR COMPOSITIONS

The terms "prevention" and "prophylaxis" are interchangeably used herein to refer to any activity that reduces the burden of mortality or morbidity from disease. Prevention and prophylaxis can occur "at primary, secondary and tertiary prevention levels." While primary prevention and prophylaxis avoid the development of a disease, secondary and tertiary levels of prevention and prophylaxis encompass activities aimed at the prevention and prophylaxis of the progression of a disease and the emergence of symptoms as well as reducing the negative impact of an already established disease by restoring function and reducing disease-related complications. Alternatively, prevention and prophylaxis can include a wide range of prophylactic therapies aimed at alleviating the severity of the particular disorder, e.g. reducing the proliferation and metastasis of tumors.

The treatment and/or prophylaxis of cancer and/or the prevention of postoperative recurrence thereof include any of the following steps, such as the surgical removal of cancer cells, the inhibition of the growth of cancerous cells, the involution or regression of a tumor, the induction of remission and suppression of occurrence of cancer, the tumor regression, and the reduction or inhibition of metastasis. Effectively treating and/or the prophylaxis of cancer decreases mortality and improves the prognosis of individuals having cancer, decreases the levels of tumor markers in the blood, and alleviates detectable symptoms accompanying cancer. For example, reduction or improvement of symptoms constitutes effectively treating and/or the prophylaxis include 10%, 20%, 30% or more reduction, or stable disease.

Since RAB6KIFL expression is up-regulated in several cancers as compared with normal tissue, the peptides of this invention or polynucleotides encoding such peptides can be used for the treatment and/or for the prophylaxis of cancer, and/or prevention of postoperative recurrence thereof. Thus, the present invention provides a pharmaceutical agent or composition for treating and/or for preventing of cancer, and/or preventing the postoperative recurrence thereof, which includes one or more of the peptides of this invention, or polynucleotides encoding the peptides as an active ingredient. Alternatively, the present peptides can be expressed on the surface of any of the foregoing exosomes or cells, such as APCs for the use as pharmaceutical agents or composition. In addition, the aforementioned cytotoxic T cells which target any of the peptides of the present invention can also be used as the active ingredient of the present pharmaceutical agents or composition. In the context of the present invention, the phrase "targeting a peptide" refers to recognizing (i.e., binding to) a complex formed between a HLA antigen and a peptide on a target cell surface with the T cell receptor, and then attacking the target cell to induce the death of the target cell.

In another embodiment, the present invention also provides the use of an active ingredient selected from among:
 (a) a peptide of the present invention,
 (b) a nucleic acid encoding such a peptide as disclosed herein in an expressible form, (c) an APC of the present invention, and (d) a cytotoxic T cells of the present invention in manufacturing a pharmaceutical composition or agent for treating cancer.

Alternatively, the present invention further provides an active ingredient selected from among:

(a) a peptide of the present invention, (b) a nucleic acid encoding such a peptide as disclosed herein in an expressible form, (c) an APC of the present invention, and (d) a cytotoxic T cells of the present invention for use in treating cancer.

Alternatively, the present invention further provides a method or process for manufacturing a pharmaceutical composition or agent for treating cancer, wherein the method or process includes the step of formulating a pharmaceutically or physiologically acceptable carrier with an active ingredient selected from among:

(a) a peptide of the present invention, (b) a nucleic acid encoding such a peptide as disclosed herein in an expressible form, (c) an APC of the present invention, and (d) a cytotoxic T cells of the present invention as active ingredients.

In another embodiment, the present invention also provides a method or process for manufacturing a pharmaceutical composition or agent for treating cancer, wherein the method or process includes the step of admixing an active ingredient with a pharmaceutically or physiologically acceptable carrier, wherein the active ingredient is selected from among:

(a) a peptide of the present invention, (b) a nucleic acid encoding such a peptide as disclosed herein in an expressible form, (c) an APC of the present invention, and (d) a cytotoxic T cells of the present invention.

Alternatively, the pharmaceutical composition or agent of the present invention may be used for either or both the prophylaxis of cancer and prevention of postoperative recurrence thereof.

The present pharmaceutical agents or compositions find use as a vaccine. In the context of the present invention, the phrase "vaccine" (also referred to as an immunogenic composition) refers to a substance that has the function to induce anti-tumor immunity upon inoculation into animals.

The pharmaceutical agents or compositions of the present invention can be used to treat and/or prevent cancers, and/or prevention of postoperative recurrence thereof in subjects or patients including human and any other mammal including, but not limited to, mouse, rat, guinea-pig, rabbit, cat, dog, sheep, goat, pig, cattle, horse, monkey, baboon, and chimpanzee, particularly a commercially important animal or a domesticated animal.

According to the present invention, oligopeptides having an amino acid sequence selected from among SEQ ID NOs: 3, 4 and 5 have been found to be HLA-A2 (A*0201)-restricted epitope peptides, that can induce potent and specific immune response. Therefore, the present pharmaceutical agents or compositions which include any of these oligopeptides with the amino acid sequences of SEQ ID NOs: 3, 4 or 5 are particularly suited for the administration to subjects whose HLA antigen is HLA-A2 (A*0201). The same applies to pharmaceutical agents or compositions which include polynucleotides encoding any of these oligopeptides.

Cancers to be treated by the pharmaceutical agents or compositions of the present invention are not limited and include all kinds of cancers wherein RAB6KIFL is involved, including for example, bladder cancer, breast cancer, cholangiocellular carcinoma, esophageal cancer, non-small cell lung cancer (NSCLC), pancreatic cancer, prostate cancer, renal carcinoma and small cell lung cancer (SCLC). In particular, the pharmaceutical agents or compositions of the present invention are preferably applied to pancreatic cancer.

The present pharmaceutical agents or compositions can contain in addition to the aforementioned active ingredients, other peptides which have the ability to induce CTLs against cancerous cells, other polynucleotides encoding the other peptides, other cells that present the other peptides, or such. Herein, the other peptides that have the ability to induce CTLs against cancerous cells are exemplified by cancer specific antigens (e.g., identified TAAs), but are not limited thereto.

If needed, the pharmaceutical agents or compositions of the present invention can optionally include other therapeutic substances as an active ingredient, so long as the substance does not inhibit the antitumoral effect of the active ingredient, e.g., any of the present peptides. For example, formulations can include anti-inflammatory agents or compositions, pain killers, chemotherapeutics, and the like. In addition to including other therapeutic substances in the medicament itself, the medicaments of the present invention can also be administered sequentially or concurrently with the one or more other pharmacologic agents or compositions. The amounts of medicament and pharmacologic agent or compositions depend, for example, on what type of pharmacologic agent(s) or compositions(s) is/are used, the disease being treated, and the scheduling and routes of administration.

It should be understood that in addition to the ingredients particularly mentioned herein, the pharmaceutical agents or compositions of this invention can include other agents or compositions conventional in the art having regard to the type of formulation in question.

In one embodiment of the present invention, the present pharmaceutical agents or compositions can be included in articles of manufacture and kits containing materials useful for treating the pathological conditions of the disease to be treated, e.g, cancer. The article of manufacture can include a container of any of the present pharmaceutical agents or compositions with a label. Suitable containers include bottles, vials, and test tubes. The containers can be formed from a variety of materials, such as glass or plastic. The label on the container should indicate the agent or compositions are used for treating or prevention of one or more conditions of the disease. The label can also indicate directions for administration and so on.

In addition to the container described above, a kit including a pharmaceutical agent or compositions of the present invention can optionally further include a second container housing a pharmaceutically-acceptable diluent. It can further include other materials desirable from a commercial and user standpoint, including other buffers, diluents, filters, needles, syringes, and package inserts with instructions for use.

The pharmaceutical compositions can, if desired, be presented in a pack or dispenser device which can contain one or more unit dosage forms containing the active ingredient. The pack can, for example, include metal or plastic foil, such as a blister pack. The pack or dispenser device can be accompanied by instructions for administration.

(1) Pharmaceutical Agents or Compositions Containing the Peptides as the Active Ingredient The peptides of this invention can be administered directly as a pharmaceutical agent or compositions or if necessary, that has been formulated by conventional formulation methods. In the latter case, in addition to the peptides of this invention, carriers, excipients, and such that are ordinarily used for drugs can be included as appropriate without particular limitations. Examples of such carriers are sterilized water, physiological saline, phosphate buffer, culture fluid and such. Furthermore, the pharmaceutical agents or compositions can contain as necessary, stabilizers, suspensions, preservatives, surfactants and such. The pharmaceutical agents or compositions of this invention can be used for anticancer purposes.

The peptides of this invention can be prepared as a combination, composed of two or more of peptides of the invention, to induce CTL in vivo. The peptide combination can take the form of a cocktail or can be conjugated to each other using standard techniques. For example, the peptides can be chemically linked or expressed as a single fusion polypeptide sequence. The peptides in the combination can be the same or different. By administering the peptides of this invention, the peptides are presented at a high density by the HLA antigens on APCs, then CTLs that specifically react toward the complex formed between the displayed peptide and the HLA antigen are induced. Alternatively, APCs that present any of the peptides of this invention on their cell surface are obtained by removing APCs (e.g., DCs) from the subjects, which are stimulated by the peptides of this invention, CTL is induced in the subjects by read-ministering these APCs (e.g., DCs) to the subjects, and as a result, aggressiveness towards the cancer cells, such as bladder cancer, breast cancer, cholangiocellular carcinoma, esophageal cancer, non-small cell lung cancer (NSCLC), pancreatic cancer, prostate cancer, renal carcinoma and small cell lung cancer (SCLC) can be increased.

The pharmaceutical agents or compositions for the treatment and/or prevention of cancer, which include a peptide of this invention as the active ingredient, can also include an adjuvant known to effectively establish cellular immunity. Alternatively, they can be administered with other active ingredients, and they can be administered by formulation into granules. An adjuvant refers to a compound that enhances the immune response against the protein when administered together (or successively) with the protein having immunological activity. Adjuvants contemplated herein include those described in the literature (Clin Microbiol Rev 1994, 7: 277-89). Examples of suitable adjuvants include, but are not limited to, aluminum phosphate, aluminum hydroxide, alum, cholera toxin, *salmonella* toxin, and such, but are not limited thereto.

Furthermore, liposome formulations, granular formulations in which the peptide is bound to few-micrometers diameter beads, and formulations in which a lipid is bound to the peptide may be conveniently used.

In some embodiments, the pharmaceutical agents or compositions of the invention may further include a component which primes CTL. Lipids have been identified as agents or compositions capable of priming CTL in vivo against viral antigens. For example, palmitic acid residues can be attached to the epsilon- and alpha-amino groups of a lysine residue and then linked to a peptide of the invention. The lipidated peptide can then be administered either directly in a micelle or particle, incorporated into a liposome, or emulsified in an adjuvant. As another example of lipid priming of CTL responses, *E. coli* lipoproteins, such as tripalmitoyl-S-glycerylcysteinylseryl-serine (P3CSS) can be used to prime CTL when covalently attached to an appropriate peptide (see, e.g., Deres et al., Nature 1989, 342: 561-4).

The method of administration can be oral, intradermal, subcutaneous, intravenous injection, or such, and systemic administration or local administration to the vicinity of the targeted sites. The administration can be performed by single administration or boosted by multiple administrations. The dose of the peptides of this invention can be adjusted appropriately according to the disease to be treated, age of the patient, weight, method of administration, and such, and is ordinarily 0.001 mg to 1000 mg, for example, 0.001 mg to 1000 mg, for example, 0.1 mg to 10 mg, and can be administered once in a few days to few months. One skilled in the art can appropriately select a suitable dose.

(2) Pharmaceutical Agents or Compositions Containing Polynucleotides as the Active Ingredient The pharmaceutical agents or compositions of the invention can also contain nucleic acids encoding the peptides disclosed herein in an expressible form. Herein, the phrase "in an expressible form" means that the polynucleotide, when introduced into a cell, will be expressed in vivo as a polypeptide that induces anti-tumor immunity. In an exemplified embodiment, the nucleic acid sequence of the polynucleotide of interest includes regulatory elements necessary for expression of the polynucleotide. The polynucleotide(s) can be equipped so to achieve stable insertion into the genome of the target cell (see, e.g., Thomas K R & Capecchi M R, Cell 1987, 51: 503-12 for a description of homologous recombination cassette vectors). See, e.g., Wolff et al., Science 1990, 247: 1465-8; U.S. Pat. Nos. 5,580,859; 5,589,466; 5,804,566; 5,739,118; 5,736,524; 5,679,647; and WO 98/04720. Examples of DNA-based delivery technologies include "naked DNA", facilitated (bupivacaine, polymers, peptide-mediated) delivery, cationic lipid complexes, and particle-mediated ("gene gun") or pressure-mediated delivery (see, e.g., U.S. Pat. No. 5,922,687).

The peptides of the present invention can also be expressed by viral or bacterial vectors. Examples of expression vectors include attenuated viral hosts, such as vaccinia or fowlpox. This approach involves the use of vaccinia virus, e.g., as a vector to express nucleotide sequences that encode the peptide. Upon introduction into a host, the recombinant vaccinia virus expresses the immunogenic peptide, and thereby elicits an immune response. Vaccinia vectors and methods useful in immunization protocols are described in, e.g., U.S. Pat. No. 4,722,848. Examples of another vector include BCG (Bacille Calmette Guerin). BCG vectors are described in Stover et al., Nature 1991, 351: 456-60. A wide variety of other vectors useful for therapeutic administration or immunization e.g., adeno and adeno-associated virus vectors, retroviral vectors, *Salmonella typhi* vectors, detoxified anthrax toxin vectors, and the like, will be apparent. See, e.g., Shata et al., Mol Med Today 2000, 6: 66-71; Shedlock et al., J Leukoc Biol 2000, 68: 793-806; Hipp et al., In Vivo 2000, 14: 571-85.

Delivery of a polynucleotide into a subject can be either direct, in which case the subject is directly exposed to a polynucleotide-carrying vector, or indirect, in which case, cells are first transformed with the polynucleotide of interest in vitro, then the cells are transplanted into the subject. Theses two approaches are known, respectively, as in vivo and ex vivo gene therapies.

For general reviews of the methods of gene therapy, see Goldspiel et al., Clinical Pharmacy 1993, 12: 488-505; Wu and Wu, Biotherapy 1991, 3: 87-95; Tolstoshev, Ann Rev Pharmacol Toxicol 1993, 33: 573-96; Mulligan, Science 1993, 260: 926-32; Morgan & Anderson, Ann Rev Biochem 1993, 62: 191-217; Trends in Biotechnology 1993, 11(5): 155-215). Methods commonly known in the art of recombinant DNA technology which can also be used for the present invention are described in eds. Ausubel et al., Current Protocols in Molecular Biology, John Wiley & Sons, NY, 1993; and Krieger, Gene Transfer and Expression, A Laboratory Manual, Stockton Press, NY, 1990.

The method of administration can be oral, intradermal, subcutaneous, intravenous injection, or such, and systemic administration or local administration to the vicinity of the targeted sites finds use. The administration can be performed by single administration or boosted by multiple administrations. The dose of the polynucleotide in the suitable carrier or cells transformed with the polynucleotide encoding the peptides of this invention can be adjusted appropriately according to the disease to be treated, age of the patient, weight, method of administration, and such, and is ordinarily 0.001 mg to 1000 mg, for example, 0.001 mg to 1000 mg, for example, 0.1 mg to 10 mg, and can be administered once every a few days to once every few months. One skilled in the art can appropriately select the suitable dose.

X. METHODS USING THE PEPTIDES, EXOSOMES, APCS AND CTLS

The peptides of the present invention and polynucleotides encoding such peptides can be used for inducing APCs and CTLs. The exosomes and APCs of the present invention can be also used for inducing CTLs. The peptides, polynucleotides, exosomes and APCs can be used in combination with any other compounds so long as the compounds do not inhibit their CTL inducibility. Thus, any of the aforementioned pharmaceutical agents or compositions of the present invention can be used for inducing CTLs, and in addition thereto, those including the peptides and polynucleotides can be also used for inducing APCs as discussed below.

(1) Method of Inducing Antigen-Presenting Cells (APCs)

The present invention provides methods of inducing APCs using the peptides of this invention or polynucleotides encoding the peptides. The induction of APCs can be performed as described above in section "VI. Antigen-presenting cells". This invention also provides a method for inducing APCs having a high level of CTL inducibility, the induction of which has been also mentioned under the item of "VI. Antigen-presenting cells", supra.

Preferably, the methods for inducing APCs include at least one step selected from among:

a: contacting APCs with the peptides of the present invention, and b: introducing the polypeptides of the present invention in an expressible form into APCs.

Such methods for inducing APCs are preferably performed in vitro or ex vivo. When the methods performed in vitro or ex vivo, APCs to be induced may be obtained from a subject to be treated or others whose HLA antigens are the same as the subject. In preferred embodiment, the APCs induced by the present methods carry HLA-A2 antigen, in particular HLA-A2 (A*0201) on its surface.

(2) Method of Inducing CTLs

Furthermore, the present invention provides methods for inducing CTLs using the peptides of this invention, polynucleotides encoding the peptides, or exosomes or APCs presenting the peptides.

The present invention also provides methods for inducing CTLs using a polynucleotide encoding a polypeptide that is capable of forming a T cell receptor (TCR) subunit recognizing (i.e., binding to) a complex of the peptides of the present invention and HLA antigens on a cell surface. Preferably, the methods for inducing CTLs include at least one step selected from among:

a: contacting a CD8-positive T cell with an antigen-presenting cell and/or an exosome that presents on its surface a complex of an HLA antigen and a peptide of the present invention, and b: introducing a polynucleotide encoding a polypeptide that is capable of forming a TCR subunit recognizing a complex of a peptide of the present invention and an HLA antigen into a CD8 positive T cell.

When the peptides of this invention are administered to a subject, CTL is induced in the body of the subject, and the strength of the immune response targeting the tumor-associated endothelia is enhanced. Alternatively, the peptides and polynucleotides encoding the peptides can be used for an ex vivo therapeutic method, in which subject-derived APCs, and CD8-positive cells, or peripheral blood mononuclear leukocytes are contacted (stimulated) with the peptides of this invention in vitro, and after inducing CTL, the activated CTL cells are returned to the subject. For example, the method can include steps of:

a: collecting APCs from subject, b: contacting with the APCs of step a, with the peptide, c: mixing the APCs of step b with $CD^{8+}$ T cells, and co-culturing for inducing CTLs, and d: collecting $CD^{8+}$ T cells from the co-culture of step c.

Alternatively, according to the present invention, use of the peptides of this invention for manufacturing a pharmaceutical composition inducing CTLs is provided. In addition, the present invention provides a method or process for manufacturing a pharmaceutical agent or composition inducing CTLs, wherein the method comprises the step of admixing or formulating the peptide of the present invention with a pharmaceutically acceptable carrier. Further, the present invention also provides the peptide of the present invention for inducing CTLs.

The $CD8^+$ T cells having cytotoxic activity obtained by step d can be administered to the subject as a vaccine. The APCs to be mixed with the $CD8^+$ T cells in above step c can also be prepared by transferring genes coding for the present peptides into the APCs as detailed above in section "VI. Antigen-presenting cells"; but are not limited thereto and any APC or exosome which effectively presents the present peptides to the T cells can be used for the present method.

Although methods and materials similar or equivalent to those described herein can be used in the practice or testing of the present invention, suitable methods and materials are described. All publications, patent applications, patents, and other references mentioned herein are incorporated by reference in their entirety. In case of conflict, the present specification, including definitions, will control. In addition, the materials, methods, and examples are illustrative only and not intended to be limiting.

The following examples are presented to illustrate the present invention and to assist one of ordinary skill in making and using the same. The examples are not intended in any way to otherwise limit the scope of the invention.

EXAMPLES

Materials and Methods cDNA Microarray Analysis

A profiling of the gene expression by a cDNA microarray analysis was done as described previously (Nakamura T, et al. Oncogene 2004; 23:2385-400). The tissue samples from pancreatic cancers and adjacent noncancerous normal pancreatic tissues were obtained from surgical specimens, and all patients provided their written informed consent to participate in this study. In FIG. 1C, the relative expression ratio was calculated by dividing the value of the expression of RAB6KIFL mRNA in cancer cells by that in normal counterpart. In FIG. 1B, the relative expression ratio of normal tissues was calculated by dividing the value of the expression of RAB6KIFL mRNA in each normal tissue by the value of the expression of RAB6KIFL mRNA in control RNA that was a mixture of equal amount of RNA samples from 40 normal tissues indicated in FIG. 1B.

Mice

HLA-A2.1 (HHD) Tgm; H-2 $D^{b-/-}$ beta 2 $m^{-/-}$ double knockout mice introduced with a human beta 2m-HLA-A2.1 (alpha 1, alpha 2)-H-2 $D^b$ (alpha 3 transmembrane cytoplasmic; HHD) monochain construct gene were generated in the Department SIDA-Retrovirus, Unite d'Immunite Cellulaire Antivirale, Institute Pasteur, France (Pascolo S, et al. J Exp Med 1997; 185:2043-51, Firat H, et al. Eur J Immunol 1999; 29:3112-21) and kindly provided by Dr. F. A. Lemonnier. The mice were maintained at the Center for Animal Resources and Development of Kumamoto University and they were handled in accordance with the animal care guidelines of Kumamoto University.

Cell Lines and HLA-Expression

The human pancreatic cancer cell line PANC1, human colon cancer cell line CaCo-2, and a TAP-deficient and HLA-A2 (A*0201)-positive cell line T2 were purchased from Riken Cell Bank (Tsukuba, Japan). The human pancreatic cancer cell line PK8 was kindly provided by the Cell Resource Center for Biomedical Research Institute of Development, Aging and Cancer, Tohoku University (Sendai, Japan). The human liver cancer cell line SKHep1 was kindly provided by Dr. Kyogo Ito, Kurume University (Kurume, Japan). The expression of HLA-A2 was examined using flow cytometry with an anti-HLA-A2 monoclonal antibody (mAb), BB7.2 (One Lambda, Inc., Canoga Park, Calif.) in order to select the HLA-A2-positive blood donors and target cell lines for the cytotoxicity assays. These cells were maintained in vitro in RPMI 1640 or DMEM medium supplemented with 10% FCS in a 5% $CO_2$ atmosphere at 37 degrees C.

Patients, Blood Samples, and Tumor Tissues.

The clinical research using PBMCs from the donors was approved by the Institutional Review Board of Kumamoto University, Kumamoto, Japan. The blood samples and the cancer and adjacent non-cancerous tissues were obtained during routine diagnostic procedures after obtaining formal written informed consents by the patients in Kumamoto University Hospital. Blood samples were also obtained from healthy donors after receiving their written informed consent. All samples were anonymous, numbered at random, and stored at −80 degrees C. until use. All patients and healthy donors were of Japanese nationality.

Reverse Transcription-PCR and Northern Blot Analysis.

Reverse transcription-PCR(RT-PCR) analysis of normal and cancer tissues and cell lines was done to evaluate the expression of RAB6KIFL at mRNA level. The primer sequences were as follows: RAB6KIFL, sense 5'-CTA-CAAGCACCCAAGGACTCT-3' (SEQ ID NO: 6) and anti-sense 5'-AGATGGAGAAGCGAATGTTT-3' (SEQ ID NO: 7) and beta-actin, sense 5'-CATCCACGAAACTACCT-TCAACT-3' (SEQ ID NO: 8) and antisense 5'-TCTCCTTA-GAGAGAAGTGGGGTG-3' (SEQ ID NO: 9), and used RT-PCR reactions consisting of initial denaturation at 94 degrees C. for 5 minutes and 32-35 amplification cycles at an annealing temperature of 58 degrees C. After normalization by beta-actin mRNA as a control, the expression of RAB6KIFL mRNA was compared in tissues and cell lines.

Western Blot Analysis and Immunohistochemical Examination.

Western blotting and immunohistochemical staining of RAB6KIFL protein were performed as described previously (Nakatsura T, et al. Biochem Biophys Res Commun 2001; 281:936-44. Yoshitake Y, et al. Clin Cancer Res 2004; 10:6437-48.). For Western blotting analyses of human normal tissues, a pre-made human adult normal tissue blot (Biochain, Hayward, Calif.) was used. The primary antibodies used herein, anti-RAB6KIFL polyclonal antibody, and monoclonal anti-b-actin antibody, were purchased from Bethyl Laboratories, Inc. (Montgomery, Tex., USA) and Sigma (Steinheim, Germany), respectively. Immunohistochemical staining of CD4 or CD8 in tissue specimens of HLA-A2.1 (HHD) Tgm immunized with the RAB6KIFL-A2-10-284 peptide was done as described previously (Matsuyoshi H, et al. 2004; 172:776-86).

Lentiviral Gene Transfer

A lentiviral vector-mediated gene transfer was performed as described previously (Imai K, et al. Clin Cancer Res 2008; 14:6487-95, Tahara-Hanaoka S, et al. Exp Hematol 2002; 30:11-7). Briefly, 17 micro-g of CSII-CMV-RfA and CSIIEF-RfA self-inactivating vectors (Miyoshi H, et al. J Virol 1998; 72: 8150-7) carrying RAB6KIFL cDNAs and 10 micro-g of pCMV-VSV-G-RSV-Rev and pCAG-HIV gp were transfected into the 293T cells grown in a 10-cm culture dish using Lipofectamine 2000 reagent (Invitrogen Corporation, Carlsbad, Calif., USA). After 60 hr of transfection, the medium was recovered and the viral particles were pelleted by ultracentrifugation (50,000×g, 2 hr). The pellet was suspended in 50 micro-L of RPMI 1640 medium and 10 micro-L of viral suspension was added to $5 \times 10^4$ SKHep1 cells, per well in a flat-bottom 96-well plate. The expression of the transfected RAB6KIFL gene was confirmed by a Western blot analysis.

Induction of RAB6KIFL-Reactive Mouse CTLs and IFN-Gamma Enzyme-Linked Immunospot Assay.

Human RAB6KIFL-derived peptides (purity>95%), carrying binding motifs for HLA-A2 (A*0201)-encoded molecules, were selected using the BIMAS software program (BioInformatics and Molecular Analysis Section, Center for information Technology, NIH, Bethesda, Md.) and 36 peptides were synthesized (American Peptide Company, CA, USA). HLA-A2-restricted HIV peptide (SLYNTYATL) (SEQ ID NO: 10) was used as an irrelevant peptide. The immunization of the mice with peptides was done as previously described (Nakatsura T, et al. Biochem Biophys Res Commun 2003; 306:16-25). The frequency of cells producing IFN-gamma/$1 \times 10^5$ CD4-spleen cells upon stimulation with syngeneic BM-DC ($1 \times 10^4$/well) pulsed with or without each peptide was analyzed by an enzyme-linked immunospot (ELISPOT) assay as previously described (Komori H, et al. Clin Cancer Res 2006; 12: 2689-97).

Induction of RAB6KIFL-reactive human CTLs.

Human RAB6KIFL-derived peptides (purity>95%), carrying binding motifs for HLA-A2 (A*0201)-encoded molecules, were selected using the BIMAS software program (BioInformatics and Molecular Analysis Section, Center for Information Technology, NIH, Bethesda, Md.) and 36 peptides were synthesized (American Peptide Company, CA, USA) (Tables 1A and B). Monocyte-derived DCs were used as antigen-presenting cells to induce CTL responses against peptides presented in the context of HLA. DCs were generated in vitro culture as described previously (Yoshitake Y, et al. Clin Cancer Res 2004; 10:6437-48, Harao M, et al. Int J Cancer 2008; in press., Imai K, et al. Clin Cancer Res 2008; in press.). Briefly, PBMCs isolated from a normal volunteer positive for HLA-A2 using Ficoll-Plaque (GE Healthcare UK, Ltd., Buckinghamshire, UK) solution were sorted to $CD8^+$ population and $CD14^+$ population with microbeads (Miltenyi Biotec, Bergisch Gladbach, Germany). To generate DCs, the $CD14^+$ population was cultured in the presence of 100 ng/mL granulocyte-macrophage colony-stimulating factor (GM-CSF; PeproTec Inc., NJ, USA) and 10 ng/mL interleukin (IL)-4 (PeproTec) in AIM-V (Invitrogen) containing 2% heat-inactivated autologous plasma. After 5 days of culture, OK-432 was added into the dish to make the DCs mature. At seven days after starting to culture the cytokine-generated DCs, they were pulsed with 20 ng/mL HLA-A2-binding peptides in the presence of 4 micro g/mL beta 2-microglobulin (Sigma-Aldrich, St. Louis, Mo., USA) for 2 h at 37 degrees C. in AIM-V. These peptides pulsed DCs were then irradiated (40 Gy) and mixed at a 1:50 ratio with autologous CD8+ T cells, obtained by positive selection of PBMCs with anti-CD8 microbeads (Miltenyi Biotec). These cultures were set up in 24-well plates, each well contained $1 \times 10^5$ peptide-pulsed DCs, $2 \times 10^6$ CD8+ T cells and 5 ng/mL human recombinant IL-7 (Wako, Osaka, Japan) in 2 mL AIM-V with 2% autologous plasma. After 2 days, these cultures were supplemented with human recombinant IL-2 (PeproTec Inc.) to a final concentration of 20 IU/mL. Two additional weekly stimulations with peptide-loaded autologous DCs using the same procedure were carried out on day 7 and 14. Six days after the last stimulation, the antigen-specific responses of induced CTLs were investigated by $^{51}$Cr release assay and IFN-gamma ELISPOT assay.

CTL Responses Against Cancer Cell Lines.

The CTLs were cocultured with each of the cancer cells, or the peptide-pulsed T2 cells, as a target cell ($5 \times 10^3$/well) at the indicated effector/target ratio and a standard $^{51}$Cr release assay was done as described previously (Yoshitake Y, et al. Clin Cancer Res 2004; 10:6437-48. Imai K, et al. Clin Cancer Res 2008; in press.). Briefly, target cells were labeled with 3.7 KBq Na$_2^{51}$Cr$^4$ (Perkin Elmer Life Sciences) for 1 h at 37 degree C. in a CO$_2$ incubator. Labeled target cells were rinsed three times, and peptide-pulsed target cells were prepared by incubating the cells with 20 micro g/mL peptide for 3 h at 37 degrees C. Target cells were mixed with effector cells in final volume of 200 micro L in flat-bottomed microtiter plates and incubated. After 6 h incubation, 50 micro L of the supernatant was collected from each well and the radioactivity was quantified using a gamma counter. The specific cytotoxicity was evaluated by calculating the percentage of specific $^{51}$Cr release.

The blocking of HLA-class I, or HLA-DR, was done as described previously (Yoshitake Y, et al. Clin Cancer Res 2004; 10:6437-48, Imai K, et al. Clin Cancer Res 2008; in press.). In brief, before the coculture of the CTLs with a cancer cell line in the $^{51}$Cr release assay or ELISPOT assay, the target cancer cells were incubated for 1 hour with 10 micro g/mL anti-class I mAb, W6/32, or 10 micro g/mL anti-HLA-DR mAb, H-DR-1, and then the effects of the mAbs on either the cytotoxic activity or the production of IFN-gamma by the CTLs were examined.

Statistical Analysis.

The two-tailed Student's t-test was used to evaluate the statistical significance of differences in the data obtained by the ELISPOT assay and in the tumor size between the treatment groups. A value of P<0.05 was considered to be significant. The statistical analysis was performed using a commercial statistical software package (SPSS for Windows, version 11.0, Chicago, Ill., USA).

Results

Identification of RAB6KIFL Gene Up-Regulated in Pancreatic Cancer and Various Malignancies Based on a cDNA Microarray.

Using a genome-wide cDNA microarray containing 27,648 genes, the gene expression profiles of 6 pancreatic cancer tissues and their adjacent normal counterparts had been previously examined. After the analysis, 6 genes were chosen. Because the relative expression ratio of these genes was more than five times higher in pancreatic cancer tissues in comparison to their normal counterparts (FIG. 1A) (Imai K, et al. Clin Cancer Res 2008; 14: 6487-95). The expression of these genes was analyzed using a cDNA microarray analysis in 29 kinds of normal tissues including 4 embryonic tissues (FIG. 1B). Consequently, RAB6KIFL/KIF20A was focused as a novel TAA of pancreatic cancer. The expression of the RAB6KIFL gene in pancreatic cancer tissues was markedly enhanced in all of the 6 patients tested (the average of the relative expression ratio: 32,000, range: 15-72,000). In addition, the RAB6KIFL gene was faintly expressed only in testis and thymus (FIG. 1B). The expression level of the RAB6KIFL gene was also enhanced in lung and bladder cancers based on the previous cDNA microarray analysis (FIG. 1C) (Nakamura T, et al. Oncogene 2004; 23:2385-400, Kitaharai 0, et al. Cancer Res 2001; 61: 3544-9, Hasegawa S, et al. Cancer Res 2002; 62: 7012-7, Kikuchi T, et al. Oncogene 2003; 22: 2192-205, Obama K, et al. Hepatology 2005; 41: 1339-48).

Expression of RAB6KIFL mRNA and Protein in Normal Organs, Cancer Cell Lines, and Pancreatic Cancer Tissues.

The expression of the RAB6KIFL gene in normal tissues at the mRNA level was analyzed using RT-PCR analysis. A semiquantitative RT-PCR analysis of RAB6KIFL in the normal tissues revealed that it was expressed only in testis (FIG. 2A). The expression of the RAB6KIFL gene was detected in the almost all pancreatic and other HLA-A2-positive cancer cell lines using an RT-PCR analysis (FIG. 2B).

Subsequently, the expression of the RAB6KIFL gene was analyzed using an RT-PCR analysis in the pancreatic cancer tissues and their adjacent normal counterparts, which were surgically resected. The expression of the RAB6KIFL gene was detected in 5 of 8 pancreatic cancer tissues, but little expression was detected in their normal counterparts (FIG. 2C). In addition, its expression was detected in the metastatic foci of the skin and peritoneum.

The expression of RAB6KIFL protein in cancerous and several normal tissues were also examined by Western blotting (FIGS. 3A, B). RAB6KIFL protein could not be detected in eight normal tissues and testis gave a very faint band that had similar mobility with that observed in a lysate of PANC1 cells (FIG. 3A). On the other hand, RAB6KIFL protein was detected in pancreatic cancer tissues of two patients examined but not in the adjacent normal tissues (FIG. 3B).

To confirm the tumor-associated overexpression of RAB6KIFL protein, many paraffin-embedded pancreatic cancer tissue specimens were then examined by immunohistochemical analyses. Strong staining of RAB6KIFL was mainly observed at the cytoplasm of cancer cells in pancreatic cancer, whereas very weak staining was observed in aciner cells and normal ductal epithelium of their normal adjacent pancreatic tissues (FIG. 4A). In addition, similar strong staining was observed in the metastatic foci of peritoneum (FIG. 4A). No staining was detected in the tissue specimens of tumor-forming pancreatitis (FIG. 4A). RAB6KIFL was not stained in the normal brain, lung, liver, kidney, stomach, small intestine, colon, spleen, skeletal muscle, skin, thymus and testis (FIG. 4B).

Prediction of HLA-A2 (A*0201) Binding Peptides Derived from RAB6KIFL

Table 1A and B show HLA-A2 (A*0201) binding peptides of the RAB6KIFL protein in the order of score of prediction high binding affinity. In total, 36 peptides with potential HLA-A2 binding activity were selected.

TABLE 1A

HLA-A2 (A*0201) binding 9mer peptides derived from RAB6KIFL

| Designation | start position | Subsequence | Score | SEQ ID |
|---|---|---|---|---|
| | 204 | LLSNEVIWL | 459 | |
| RAB6KIFL-A2-9-12 | 12 | LLSDDDVVV | 199 | SEQ ID NO: 3 |
| | 715 | KMLEPPPSA | 191 | |
| | 750 | KLGESLQSA | 164 | |
| | 300 | SIWISFFEI | 131 | |
| | 38 | NLLSDCSVV | 106 | |
| | 688 | QLQEVKAKL | 88 | |
| | 695 | KLQQCKAEL | 75 | |
| RAB6KIFL-A2-9-809 | 809 | CIAEQYHTV | 59 | SEQ ID NO: 4 |
| | 11 | GLLSDDDVV | 52 | |
| | 436 | TLGRCIAAL | 49 | |
| | 179 | ILPRSLALI | 41 | |
| | 183 | SLALIFNSL | 41 | |
| | 625 | KLNILKESL | 37 | |
| | 781 | ILIKQDQTL | 36 | |
| | 231 | GLQEEELST | 31 | |
| | 494 | TLHVAKFSA | 29 | |
| | 556 | SMYGKEELL | 24 | |
| | 788 | TLAELQNNM | 20 | |
| | 209 | VIWLDSKQI | 20 | |

Start position indicates the number of amino acid from the N-terminus of RAB6KIFL.
Binding score is derived in Materials and Methods.

TABLE 1B

HLA-A2 (A*0201) binding 10mer peptides derived from RAB6KIFL

| Designation | start position | Subsequence | Score | SEQ ID |
|---|---|---|---|---|
| | 654 | LLQEARQQSV | 485 | |
| | 788 | TLAELQNNMV | 285 | |
| | 742 | RLLRTELQKL | 182 | |
| | 39 | LLSDCSVVST | 119 | |
| | 11 | GLLSDDDVVV | 106 | |
| | 400 | KISELSLCDL | 97 | |
| | 573 | LLLKERQEKL | 66 | |
| | 97 | VLQAPKDSFA | 46 | |
| RAB6KIFL-A2-10-284 | 284 | AQPDTAPLPV | 29 | SEQ ID NO: 5 |
| | 132 | GQASFFNLTV | 27 | |
| | 625 | KLNILKESLT | 26 | |
| | 382 | SIFSIRILHL | 25 | |

TABLE 1B-continued

HLA-A2 (A*0201) binding 10mer peptides derived from RAB6KIFL

| Designation | start position | Subsequence | Score | SEQ ID |
|---|---|---|---|---|
| | 203 | PLLSNEVIWL | 22 | |
| | 455 | NLVPFRDSKL | 21 | |
| | 506 | QLVHAPPMQL | 21 | |
| | 98 | LQAPKDSFAL | 21 | |
| | 66 | KVYLRVRPLL | 21 | |

Start position indicates the number of amino acid from the N-terminus of RAB6KIFL.
Binding score is derived in Materials and Methods.

Identification of RAB6KIFL-Derived and HLA-A2-Restricted Mouse CTL Epitopes Using HLA-A2.1 (HHD) Transgenic Mice To identify the RAB6KIFL-derived and HLA-A2-restricted CTL epitopes, 36 different candidate peptides were selected. Each consisted of 9 or 10 amino-acids that have high predicted binding scores to HLA-A2 (A*0201), the most common HLA-allelic product worldwide, based on the HLA peptide binding prediction algorism provided by the NIH BIMAS (Tables 1A, B). To determine which could induce peptide-reactive CTLs, the CD4⁻ spleen cells isolated from HLA-A2.1 (HHD) Tgm, immunized i.p. twice with BM-DCs pulsed with the twelve sets of the mixture of three kinds of peptides selected from these 36 peptides, were again stimulated in vitro with BM-DCs pulsed with each peptide. The results showed that the CD4⁻ spleen cells, stimulated with RAB6KIFL-A2-9-12, RAB6KIFL-A2-9-809, and RAB6KIFL-A2-10-284 peptide, produced a significant amount of IFN-gamma in a peptide-specific manner in an ELISPOT assay (FIG. 5A). These CD4⁻ spleen cells ($2 \times 10^4$) showed 149.0 plus/minus 22.2 spot counts/well in response to the BM-DCs pulsed with the RAB6KIFL-A2-9-12 peptide, whereas they showed 32.6 plus/minus 9.9 spot counts/well in the presence of the BM-DCs without peptide loading ($P<0.01$). Likewise, the CD4⁻ spleen cells stimulated with BM-DCs pulsed with RAB6KIFL-A2-9-809 peptide showed 117.2 plus/minus 23.4 spot counts/well, whereas they showed 51.4 plus/minus 7.8 spot counts/well in the presence of BM-DCs without peptide loading ($P<0.01$). Moreover, the CD4⁻ spleen cells stimulated with BM-DCs pulsed with RAB6KIFL-A2-10-284 peptide also showed 141.2 plus/minus 5.5 spot counts/well, whereas they showed 19.2 plus/minus 5.2 spot counts/well in the presence of BM-DCs without peptide loading ($P<0.01$). No significant peptide-specific response was observed with the other peptides. These results suggest that the RAB6KIFL-A2-9-12, RAB6KIFL-A2-9-809 and RAB6KIFL-A2-10-284 peptides could be the HLA-A2 restricted CTL epitope peptides in the HLA-A2.1 (HHD) Tgm, and those peptides were expected to be epitopes for human CTLs.

No Autoimmune Phenomenon Induced by the Immunization with Epitope Peptide, RAB6KIFL-A2-9-809, in HLA-A2.1 (HHD) Tgm It is very important to investigate whether the immunization with RAB6KIFL peptide induce an autoimmune reaction or not. We thus performed the immunohistochemical analysis of several vital organs with anti-CD4 and anti-CD8 mAb in HLA-A2 (HHD) Tgm after two-times vaccination with RAB6KIFL-A2-9-809 peptide, of which amino-acid sequences were completely conserved between human and mouse RAB6KIFL. As a result, no pathologic change, such as lymphocyte infiltration or tissue destruction suggesting autoimmunity was observed (FIG. 5B). The abnormalities frequently observed in mice affected with autoimmune diseases such as abnormal hair and skin, diarrhea and weight loss were also not observed in these mice. These results indicate that lymphocytes stimulated with RAB6KIFL-A2-9-809 peptide did not attack the normal tissues at least in HLA-A2 Tgm.

Induction of RAB6KIFL-Reactive CTLs from PBMCs of HLA-A2 (A*0201)-Positive Healthy Donors The generation of RAB6KIFL-specific CTLs was attempted from the PBMCs of healthy donors positive for HLA-A2 (A*0201) by the stimulation with the RAB6KIFL-A2-9-12 (SEQ ID NO: 3), RAB6KIFL-A2-9-809 (SEQ ID NO: 4) and RAB6KIFL-A2-10-284 (SEQ ID NO: 5) peptides. PBMCs were isolated form HLA-A2-positive healthy donors, and the CD8⁺ T cells sorted from the PBMCs were incubated with the autologous monocyte-derived DCs pulsed with each peptide. After three times stimulations, the cytotoxic activity against the peptide-pulsed T2 cells was examined by a $^{51}$Cr release assay (FIG. 6A) and an IFN-gamma ELISPOT assay (data not shown). The CTLs induced from the PBMCs of two healthy donors exhibited cytotoxic activity to the T2 cells pulsed with RAB6KIFL-A2-9-12 (SEQ ID NO: 3), RAB6KIFL-A2-9-809 (SEQ ID NO: 4) or RAB6KIFL-A2-10-284 (SEQ ID NO: 5) peptide, but not to the T2 cells pulsed with irrelevant and HLA-A2-restricted HIV peptide, or without peptide loading. Similar responses were observed in other donors (data not shown). These results indicate that these CTLs had a peptide-specific cytotoxicity.

Subsequently, it was investigated whether these CTLs were able to kill human cancer cell lines expressing RAB6KIFL and HLA-A2 (A*0201). As shown in FIG. 6B, the RAB6KIFL-reactive CTLs stimulated with RAB6KIFL-A2-9-12 (left), RAB6KIFL-A2-9-809 (middle), or RAB6KIFL-A2-10-284 (right) peptide exhibited cytotoxicity to PANC1 (RAB6KIFL⁺, HLA-A2⁺), CaCo-2 (RAB6KIFL HLA-A2⁺), but not to PK8 (RAB6KIFL⁺, HLA-A2⁻) in healthy donors.

Furthermore, SKHep1/RAB6KIFL (RAB6KIFL$^{high}$, HLA-A2⁺), the SKHep1 (RAB6KIFL$^{low}$, HLA-A2⁺) cells transfected with the RAB6KIFL gene (FIG. 2B), were used as target cells to confirm that these peptides were processed naturally from the RAB6KIFL protein in the cancer cells. As shown in FIG. 6C, the CTLs induced by stimulation with RAB6KIFL-A2-9-12 (left), RAB6KIFL-A2-9-809 (middle), and RAB6KIFL-A2-10-284 (right) peptide exhibited cytotoxicity against SKHep1/RAB6KIFL, but not against SKHep1/Mock. These results suggest that these peptides could be naturally processed and expressed on the surface of cancer cells in the context of HLA-A2 molecules.

To confirm that the induced CTLs recognized the target cells in an HLA-class I-restricted manner, an HLA-class I blocking assay was performed by using the mAb against HLA-class T (W6/32) was used to block the recognition of cancer cells by the CTLs (FIG. 6D). As a result, the anti-HLA-class I antibody could markedly inhibit the IFN-gamma production stimulated with PANC1 cells in an ELISPOT assay of the CTLs generated by stimulation with RAB6KIFL-A2-9-12 (left), RAB6KIFL-A2-9-809 (middle), or RAB6KIFL-A2-10-284 (right) peptide, with statistical significance (FIG. 6D, P<0.01). These results clearly indicate that these induced CTLs recognized the target cells expressing RAB6KIFL in an HLA-class I-restricted manner.

Discussion

Figure 2:
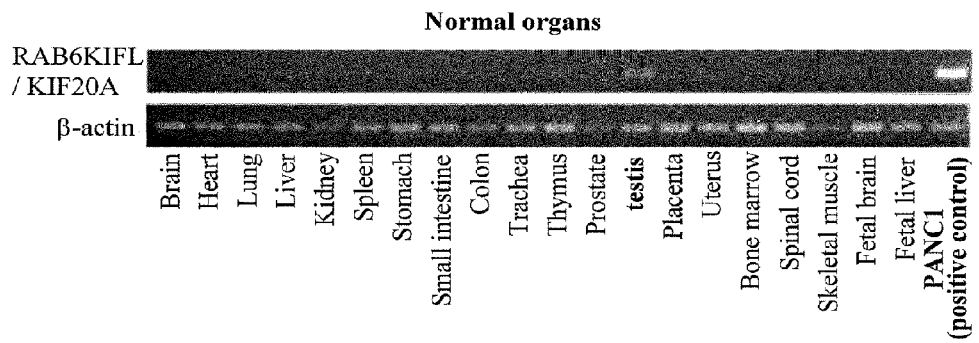
FIG. 2 depicts the analyses of RAB6KIFL mRNA expressed in human normal tissues, cancer cell lines, and cancer tissues. A depicts the expression of RAB6KIFL mRNA was investigated in various normal tissues by using RT-PCR analysis. RAB6KIFL mRNA was faintly expressed only in testis. B depicts the RT-PCR analysis of the RAB6KIFL expression in various cancer cell lines. C depicts the RT-PCR analysis of the RAB6KIFL expression in pancreatic tumor tissues (T), and their normal counterparts (N). The expression of the RAB6KIFL gene was detected in 5 of 8 pancreatic cancer tissues. In contrast, little expression was detected in their normal counterparts.
Figure 2:
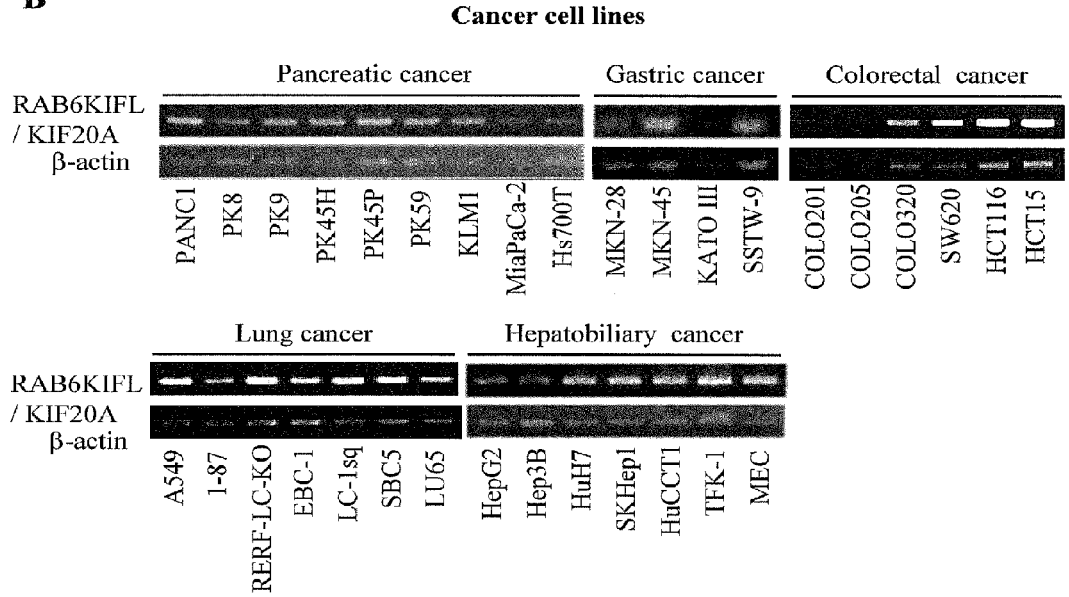
Figure 2:
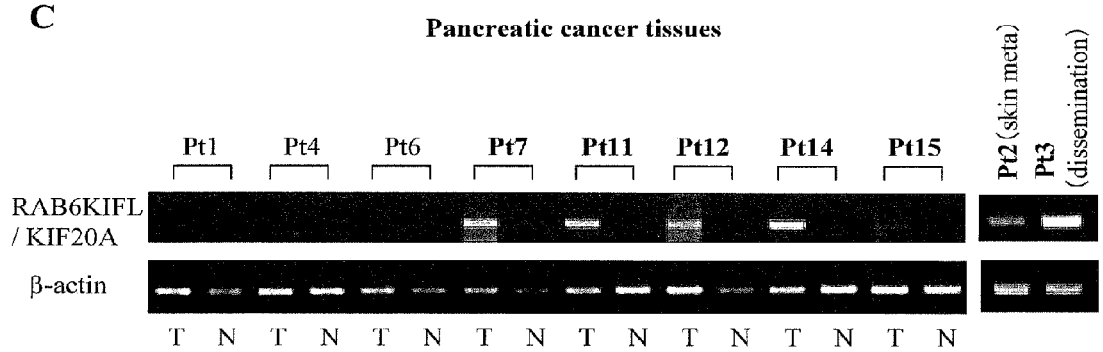
Figure 3:
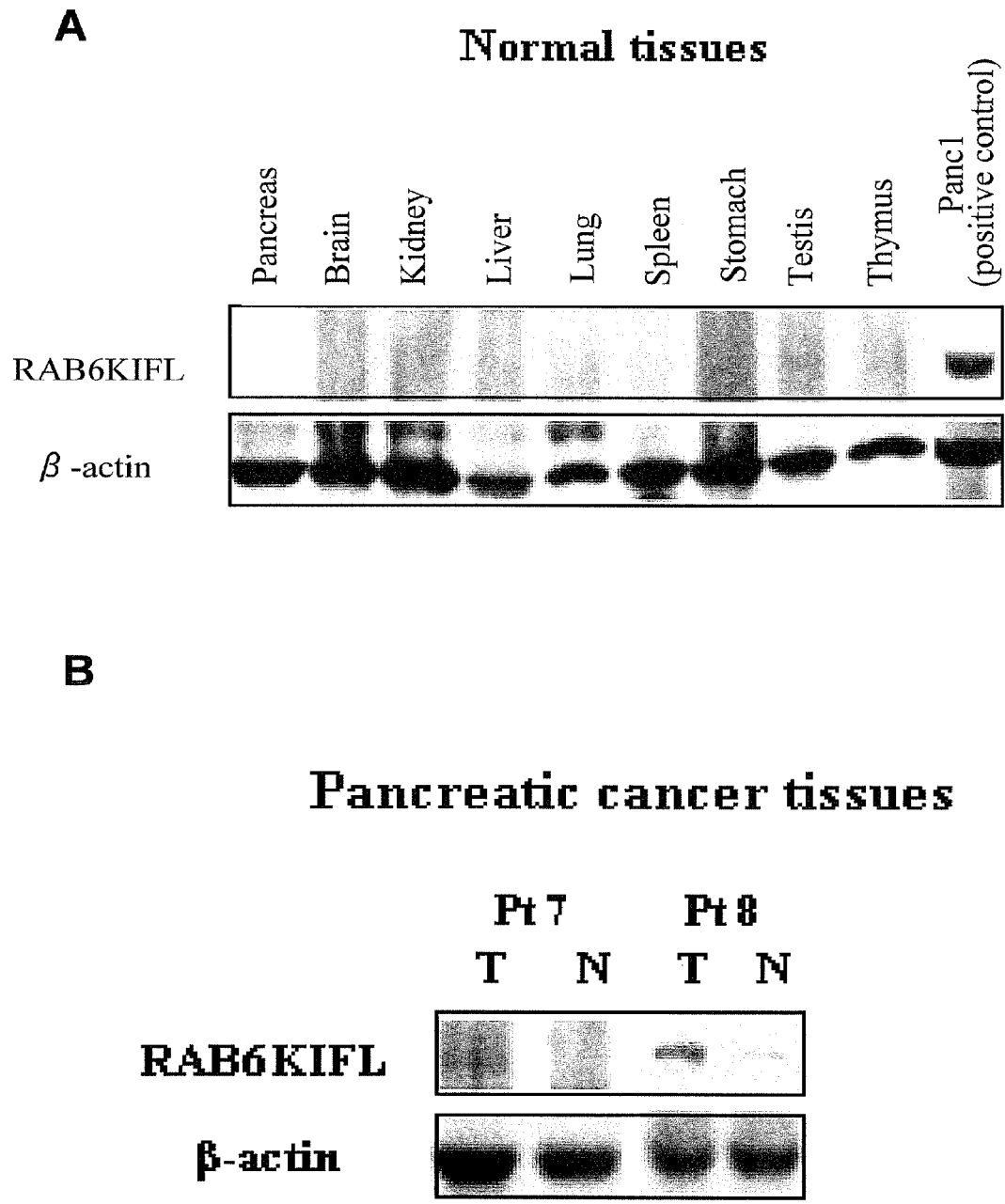
FIG. 3 depicts pancreatic cancer-specific overexpression of RAB6KIFL protein detected by Western blotting analyses. A depicts that RAB6KIFL protein was not detected in eight normal tissues, whereas the testis gave a faint band that had a similar mobility with that observed in PANC1 cell lysate. B depicts that, in two pancreatic cancer patients, RAB6KIFL protein was detected in cancer tissues (T) but not in adjacent normal tissues (N). Anti-beta-actin blotting was also performed to monitor equal protein loading.
Figure 4:
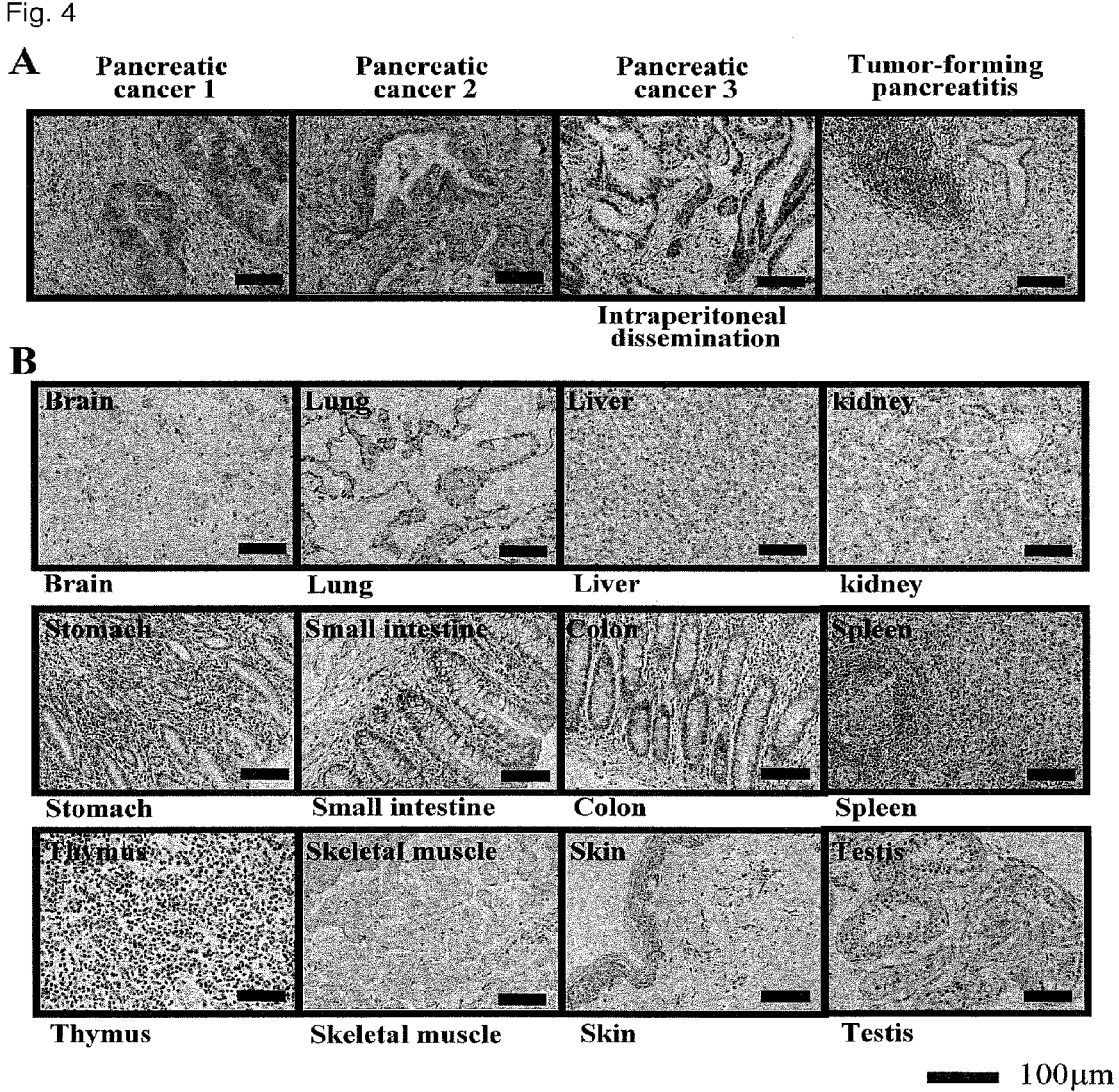
FIG. 4 depicts immunohistochemical analyses of RAB6KIFL protein in pancreatic cancer (A) and various normal tissues (B). A depicts strong staining of RAB6KIFL was mainly observed at the cytoplasm and nuclei of cancer cells in 6 of 9 cases, whereas very weak staining was observed in aciner cells and normal ductal epithelium of their normal adjacent pancreatic tissues. Similar strong staining was observed in the metastatic foci of the peritoneum. Little staining was detected in tumor-forming pancreatitis. B depicts RAB6KIFL was not stained in the normal brain, lung, liver, kidney, stomach, small intestine, colon, spleen, skeletal muscle, skin, and thymus. A possible faint staining was observed in testis. Positive staining signals are shown in brown color. The scale bars represent 100 micrometers.

According to the example, it was shown that RAB6KIFL is a TAA as a promising target of anticancer immunotherapy for pancreatic cancer. To establish anticancer immunotherapy, it is important to identify the TAAs that are strongly expressed in tumor cells but not in the normal cells. The cDNA microarray analysis showed that RAB6KIFL mRNA was overexpressed in pancreatic cancer cells (Imai K, Hirata S, Irie A, Senju S, Ikuta Y, Yokomine K, Harao M, Inoue M, Tsunoda T, Nakatsuru S, Nakagawa H, Nakamura Y, et al. Clin Cancer Res 2008; 14: 6487-95) and barely expressed in their normal counterparts and many normal adult tissues except for the testis and thymus (FIG. 1B). In addition, the RAB6KIFL gene was also overexpressed in lung and bladder cancers as well as in pancreatic cancer (FIG. 1C). In the RT-PCR analysis demonstrated that RAB6KIFL mRNA was frequently expressed in several cancer cell lines and pancreatic cancer tissues, but not in adult normal tissues including bone marrow except for testis (FIG. 2). Similarly, Western blotting analyses and immunohistochemical analyses revealed that RAB6KIFL protein was detected in pancreatic cancer cells, but not in their normal counterparts and normal adult tissues including thymus except for testis (FIGS. 3, 4). These observations support a characteristic of RAB6KIFL as a cancer testis-like TAA at a protein level.

For the identification of TAAs as useful targets for anticancer immunotherapy, another key point is to select the antigens which are indispensable for the proliferation, invasion, metastasis, and survival of cancer cells. Recently, Taniuchi et al. reported that RAB6KIFL is involved in pancreatic carcinogenesis (Taniuchi K, et al. Cancer Res 2005; 65:105-12), in addition to its previously described role in membrane traffic (Echard A, et al. Science 1998; 279:580-5) and cytokinesis (Fontijn R D, et al. Mol Cell Biol 2001; 21:2944-55, Hill E, Clarke M, Barr F A. EMBO J. 2000; 19:5711-9). They showed that the down-regulation of endogenous RAB6KIFL in pancreatic cancer cells by small interfering RNA results in a drastic attenuation of cancer cell growth through the interaction with disc, large homologue 5 (DLG5), a cargo protein of RAB6KIFL (Taniuchi K, et al. Cancer Res 2005; 65:105-12), suggesting that RAB6KIFL thus appears to play a critical role in pancreatic carcinogenesis and would therefore be a potentially useful target of anticancer immunotherapy.

The potential of RAB6KIFL as an immunotherapeutic target was verified herein by identifying the HLA-A2-restricted epitope peptides and evaluating their immunogenicity. The experiment using HLA-A2 (HHD) Tgm identified three HLA-A2-restricted RAB6KIFL epitope peptides which could stimulate the generation of HLA-A2-restricted mouse CTLs by the vaccination with the 36 candidate peptides predicted to have binding affinity to HLA-A2 (A*0201) by the BIMAS algorithm, without causing autoimmune phenomenon such as lymphocyte infiltration or tissue destruction (FIG. 5). Furthermore, the RAB6KIFL-reactive CTLs could be generated from PBMCs stimulated with all of these three peptides in three independent healthy donors (FIG. 6). These CTLs could kill not only the T2 cells pulsed with its cognate peptide, but also the cancer cell lines expressing both RAB6KIFL and HLA-A2. The antigen-specificity of CTLs to these peptides was confirmed by the findings that these CTLs exhibited cytotoxicity to SKHep1 cells transfected with human RAB6KIFL gene, but not to the mock-transfected SKHep1. These data suggest that these RAB6KIFL peptides (RAB6KIFL-A2-9-12, RAB6KIFL-A2-9-809, and RAB6KIFL-A2-10-284) are naturally processed from RAB6KIFL protein in cancer cells and presented onto the cell surface together with HLA-A2 molecules to be recognized by the CTLs. In addition, it would be possible that the RAB6KIFL-A2-9-809 peptide can be more effectively processed from RAB6KIFL protein in comparison to the RAB6KIFL-A2-9-12 and RAB6KIFL-A2-10-284 peptides in cancer cells, because the RAB6KIFL-A2-9-809 peptide-induced CTLs exhibited stronger cytotoxicity directed against cancer cells expressing both RAB6KIFL and HLA-A2 in comparison to cytotoxicity mediated by CTLs induced by stimulation with the RAB6KIFL-A2-9-12 or the RAB6KIFL-A2-10-284 peptides.

HLA-A2.1 (HHD) Tgm that lacked expression of endogenous mouse H-$2^b$-encoded class I molecules were used to identify HLA-A2-restricted CTL epitope peptides of RAB6KIFL. HLA-A2.1 (HHD) Tgm was reported to be a versatile animal model for the preclinical evaluation of peptide-based immunotherapy (Imai K, et al. Clin Cancer Res 2008; 14:6487-95, Komori H, et al. Clin Cancer Res 2006; 12:2689-97, Harao M, et al. Int J Cancer 2008; 123: 2616-25, Pascolo S, et al. J Exp Med 1997; 185: 2043-51, Firat H, et al. Eur J Immunol 1999; 29: 3112-21).

To avoid the adverse effects induced by vaccination of TAAs, RAB6KIFL was selected as a target which was barely expressed in adult normal tissues. However, it was very important to determine whether vaccination of RAB6KIFL could induce autoimmune diseases either during or after anticancer immunotherapy. Herein, the amino-acid sequences of two of three epitope peptides are not conserved between human and mouse (RAB6KIFL-A2-9-12, human: LLSDDVVV (SEQ ID NO: 3), mouse: LLSDEDVVD (SEQ ID NO: 11); RAB6KIFL-A2-10-284, human: AQPDTAPLPV (SEQ ID NO: 5), mouse: AQPDTVPVSV) (SEQ ID NO: 12). Therefore, the autoimmune phenomenon in HLA-A2 Tgm was investigated after two-times vaccination with RAB6KIFL-A2-9-809 peptide in which amino-acid sequences were completely conserved between in human and mouse. One of the advantages of using HLA-A2 Tgm is that the possibility of autoimmune phenomenon could be investigated in vivo. Of course, because the number of normal tissues investigated herein is limited, it is not possible to exclude the possible expression of RAB6KIFL in some normal tissues that has not been investigated herein. Therefore, it must be careful about induction of autoimmune diseases when utilizing RAB6KIFL peptides for cancer immunotherapy.

In conclusion, the current results suggest that RAB6KIFL is a TAA containing epitope peptides that can elicit CTLs reactive to cancer cells expressing both RAB6KIFL and HLA-A2. Since RAB6KIFL is highly expressed in a wide range of human malignancies, RAB6KIFL is therefore a promising target for peptide-based immunotherapy for the treatment of a broad-spectrum of malignancies, especially pancreatic cancer. Further investigation of the capability for induction of RAB6KIFL-specific CTLs in pancreatic cancer patients thus remains an issue of great importance for clinical application.

INDUSTRIAL APPLICABILITY

The present invention describes new TAAs, particularly those derived from RAB6KIFL that induce potent and specific anti-tumor immune responses and have applicability to a wide array of cancer types. Such TAAs warrant further development as peptide vaccines against diseases associated with RAB6KIFL, e.g., cancers such as bladder cancer, cervical cancer, cholangiocellular carcinoma, esophagus cancer, gastric cancer, non-small cell lung cancer (NSCLC), osteosarcoma, pancreatic cancer, renal carcinoma and soft tissue tumor.

While the present invention is herein described in detail and with reference to specific embodiments thereof, it is to be understood that the foregoing description is exemplary and explanatory in nature and is intended to illustrate the invention and its preferred embodiments. Through routine experimentation, one skilled in the art will readily recognize that various changes and modifications can be made therein without departing from the spirit and scope of the invention, the metes and bounds of which are defined by the appended claims.

The invention claimed is:

1. An isolated oligopeptide, wherein the oligopeptide consists
of an amino acid sequence selected from the group consisting of SEQ ID NOs: 3, 4 and 5 in which 1 or 2 amino acids are substituted, wherein the substitution is selected from the group consisting of:
(a) the second amino acid from the N-terminus is substituted with leucine or methionine and
(b) the C-terminal amino acid is substituted with leucine, wherein the oligopeptide has cytotoxic T lymphocyte (CTL) inducibility.

2. A pharmaceutical composition for treating cancer, wherein the composition comprises a pharmaceutically acceptable carrier and one or more oligopeptides consisting of the amino acid sequence of SEQ ID NO: 3, 4, or 5, or one or more oligopeptides of claim 1, wherein the pharmaceutically acceptable carrier is sterilized water, physiological saline, or phosphate buffer.

3. The pharmaceutical composition of claim 2, which is formulated for the administration to a subject whose HLA antigen is HLA-A2.

4. The pharmaceutical composition of claim 2, wherein the cancer is selected from the group consisting of bladder cancer, breast cancer, cholangiocellular carcinoma, esophageal cancer, non-small cell lung cancer (NSCLC), pancreatic cancer, prostate cancer, renal carcinoma and small cell lung cancer (SCLC).

5. A pharmaceutical composition for inducing a CTL, wherein the composition comprises a pharmaceutically acceptable carrier and one or more oligopeptides consisting of the amino acid sequence of SEQ ID NO: 3, 4, or 5, or one or more oligopeptides of claim 1, wherein the pharmaceutically acceptable carrier is sterilized water, physiological saline, or phosphate buffer.

* * * * *

```
                           SEQUENCE LISTING

<160> NUMBER OF SEQ ID NOS: 12

<210> SEQ ID NO 1
<211> LENGTH: 3471
<212> TYPE: DNA
<213> ORGANISM: Homo sapiens
<220> FEATURE:
<221> NAME/KEY: CDS
<222> LOCATION: (497)..(3169)

<400> SEQUENCE: 1 ttttcccct  taagacaaag  caagcaccct  aaaccagtta  ccctgtgcac  tcctgttaag      60
attgttgcta  aggaaggaca  ggagttggct  gctgaagcct  caagatttcc  tttaggctct    120
taggtaagaa  atgtctaagg  ttcaaggaaa  aaggttaagt  tggaagaatc  ccaggcaaaa    180
taagtgcgaa  tccacgacag  ttggtaaccc  ggacccacat  tagaactcag  aggtcaagca    240
gaagcgaacg  actggaattc  cagtcaggcc  cgccccettt  ccttacgcgg  attggtagct    300
gcaggcttcc  ctatctgatt  ggccgaacga  acgcagcgcg  taatttaaaa  tattgtatct    360
gtaacaaagc  tgcacctcgt  gggcggagtt  gtgctctgcg  gctgcgaaag  tccagcttcg    420
gcgactaggt  gtgagtaagc  cagtatccca  ggaggagcaa  gtggcacgtc  ttcggaccta    480
ggctgcccct  gccgtc atg  tcg caa  ggg atc  ctt tct  ccg cca  gcg ggc ttg    532
               Met Ser Gln Gly Ile Leu Ser Pro Pro Ala Gly Leu
                 1               5                   10 ctg tcc gat gac gat gtc gta gtt tct ccc atg ttt gag tcc aca gct            580
Leu Ser Asp Asp Asp Val Val Val Ser Pro Met Phe Glu Ser Thr Ala
        15                  20                  25 gca gat ttg ggg tct gtg gta cgc aag aac ctg cta tca gac tgc tct            628
Ala Asp Leu Gly Ser Val Val Arg Lys Asn Leu Leu Ser Asp Cys Ser
    30                  35                  40 gtc gtc tct acc tcc cta gag gac aag cag cag gtt cca tct gag gac            676
Val Val Ser Thr Ser Leu Glu Asp Lys Gln Gln Val Pro Ser Glu Asp
45                  50                  55                  60 agt atg gag aag gtg aaa gta tac ttg agg gtt agg ccc ttg tta cct            724
Ser Met Glu Lys Val Lys Val Tyr Leu Arg Val Arg Pro Leu Leu Pro
                65                  70                  75 tca gag ttg gaa cga cag gaa gat cag ggt tgt gtc cgt att gag aat            772
Ser Glu Leu Glu Arg Gln Glu Asp Gln Gly Cys Val Arg Ile Glu Asn
            80                  85                  90 gtg gag acc ctt gtt cta caa gca ccc aag gac tct ttt gcc ctg aag            820
Val Glu Thr Leu Val Leu Gln Ala Pro Lys Asp Ser Phe Ala Leu Lys
        95                 100                 105 agc aat gaa cgg gga att ggc caa gcc aca cac agg ttc acc ttt tcc            868
Ser Asn Glu Arg Gly Ile Gly Gln Ala Thr His Arg Phe Thr Phe Ser
    110                 115                 120
```

```
cag atc ttt ggg cca gaa gtg gga cag gca tcc ttc ttc aac cta act    916
Gln Ile Phe Gly Pro Glu Val Gly Gln Ala Ser Phe Phe Asn Leu Thr
125             130                 135                 140 gtg aag gag atg gta aag gat gta ctc aaa ggg cag aac tgg ctc atc    964
Val Lys Glu Met Val Lys Asp Val Leu Lys Gly Gln Asn Trp Leu Ile
        145                 150                 155 tat aca tat gga gtc act aac tca ggg aaa acc cac acg att caa ggt   1012
Tyr Thr Tyr Gly Val Thr Asn Ser Gly Lys Thr His Thr Ile Gln Gly
                160                 165                 170 acc atc aag gat gga ggg att ctc ccc cgg tcc ctg gcg ctg atc ttc   1060
Thr Ile Lys Asp Gly Gly Ile Leu Pro Arg Ser Leu Ala Leu Ile Phe
            175                 180                 185 aat agc ctc caa ggc caa ctt cat cca aca cct gat ctg aag ccc ttg   1108
Asn Ser Leu Gln Gly Gln Leu His Pro Thr Pro Asp Leu Lys Pro Leu
        190                 195                 200 ctc tcc aat gag gta atc tgg cta gac agc aag cag atc cga cag gag   1156
Leu Ser Asn Glu Val Ile Trp Leu Asp Ser Lys Gln Ile Arg Gln Glu
205                 210                 215                 220 gaa atg aag aag ctg tcc ctg cta aat gga ggc ctc caa gag gag gag   1204
Glu Met Lys Lys Leu Ser Leu Leu Asn Gly Gly Leu Gln Glu Glu Glu
                225                 230                 235 ctg tcc act tcc ttg aag agg agt gtc tac atc gaa agt cgg ata ggt   1252
Leu Ser Thr Ser Leu Lys Arg Ser Val Tyr Ile Glu Ser Arg Ile Gly
            240                 245                 250 acc agc acc agc ttc gac agt ggc att gct ggg ctc tct tct atc agt   1300
Thr Ser Thr Ser Phe Asp Ser Gly Ile Ala Gly Leu Ser Ser Ile Ser
        255                 260                 265 cag tgt acc agc agt agc cag ctg gat gaa aca agt cat cga tgg gca   1348
Gln Cys Thr Ser Ser Ser Gln Leu Asp Glu Thr Ser His Arg Trp Ala
270                 275                 280 cag cca gac act gcc cca cta cct gtc ccg gca aac att cgc ttc tcc   1396
Gln Pro Asp Thr Ala Pro Leu Pro Val Pro Ala Asn Ile Arg Phe Ser
285                 290                 295                 300 atc tgg atc tca ttc ttt gag atc tac aac gaa ctg ctt tat gac cta   1444
Ile Trp Ile Ser Phe Phe Glu Ile Tyr Asn Glu Leu Leu Tyr Asp Leu
                305                 310                 315 tta gaa ccg cct agc caa cag cgc aag agg cag act ttg cgg cta tgc   1492
Leu Glu Pro Pro Ser Gln Gln Arg Lys Arg Gln Thr Leu Arg Leu Cys
            320                 325                 330 gag gat caa aat ggc aat ccc tat gtg aaa gat ctc aac tgg att cat   1540
Glu Asp Gln Asn Gly Asn Pro Tyr Val Lys Asp Leu Asn Trp Ile His
        335                 340                 345 gtg caa gat gct gag gag gcc tgg aag ctc cta aaa gtg ggt cgt aag   1588
Val Gln Asp Ala Glu Glu Ala Trp Lys Leu Leu Lys Val Gly Arg Lys
350                 355                 360 aac cag agc ttt gcc agc acc cac ctc aac cag aac tcc agc cgc agt   1636
Asn Gln Ser Phe Ala Ser Thr His Leu Asn Gln Asn Ser Ser Arg Ser
365                 370                 375                 380 cac agc atc ttc tca atc agg atc cta cac ctt cag ggg gaa gga gat   1684
His Ser Ile Phe Ser Ile Arg Ile Leu His Leu Gln Gly Glu Gly Asp
                385                 390                 395 ata gtc ccc aag atc agc gag ctg tca ctc tgt gat ctg gct ggc tca   1732
Ile Val Pro Lys Ile Ser Glu Leu Ser Leu Cys Asp Leu Ala Gly Ser
            400                 405                 410 gag cgc tgc aaa gat cag aag agt ggt gaa cgg ttg aag gaa gca gga   1780
Glu Arg Cys Lys Asp Gln Lys Ser Gly Glu Arg Leu Lys Glu Ala Gly
        415                 420                 425 aac att aac acc tct cta cac acc ctg ggc cgc tgt att gct gcc ctt   1828
Asn Ile Asn Thr Ser Leu His Thr Leu Gly Arg Cys Ile Ala Ala Leu
430                 435                 440
```

```
cgt caa aac cag cag aac cgg tca aag cag aac ctg gtt ccc ttc cgt    1876
Arg Gln Asn Gln Gln Asn Arg Ser Lys Gln Asn Leu Val Pro Phe Arg
445                 450                 455                 460 gac agc aag ttg act cga gtg ttc caa ggt ttc ttc aca ggc cga ggc    1924
Asp Ser Lys Leu Thr Arg Val Phe Gln Gly Phe Phe Thr Gly Arg Gly
                465                 470                 475 cgt tcc tgc atg att gtc aat gtg aat ccc tgt gca tct acc tat gat    1972
Arg Ser Cys Met Ile Val Asn Val Asn Pro Cys Ala Ser Thr Tyr Asp
480                 485                 490 gaa act ctt cat gtg gcc aag ttc tca gcc att gct agc cag ctt gtg    2020
Glu Thr Leu His Val Ala Lys Phe Ser Ala Ile Ala Ser Gln Leu Val
                495                 500                 505 cat gcc cca cct atg caa ctg gga ttc cca tcc ctg cac tcg ttc atc    2068
His Ala Pro Pro Met Gln Leu Gly Phe Pro Ser Leu His Ser Phe Ile
510                 515                 520 aag gaa cat agt ctt cag gta tcc ccc agc tta gag aaa ggg gct aag    2116
Lys Glu His Ser Leu Gln Val Ser Pro Ser Leu Glu Lys Gly Ala Lys
525                 530                 535                 540 gca gac aca ggc ctt gat gat gat att gaa aat gaa gct gac atc tcc    2164
Ala Asp Thr Gly Leu Asp Asp Asp Ile Glu Asn Glu Ala Asp Ile Ser
                545                 550                 555 atg tat ggc aaa gag gag ctc cta caa gtt gtg gaa gcc atg aag aca    2212
Met Tyr Gly Lys Glu Glu Leu Leu Gln Val Val Glu Ala Met Lys Thr
                560                 565                 570 ctg ctt ttg aag gaa cga cag gaa aag cta cag ctg gag atg cat ctc    2260
Leu Leu Leu Lys Glu Arg Gln Glu Lys Leu Gln Leu Glu Met His Leu
                575                 580                 585 cga gat gaa att tgc aat gag atg gta gaa cag atg caa cag cgg gaa    2308
Arg Asp Glu Ile Cys Asn Glu Met Val Glu Gln Met Gln Gln Arg Glu
590                 595                 600 cag tgg tgc agt gaa cat ttg gac acc caa aag gaa cta ttg gag gaa    2356
Gln Trp Cys Ser Glu His Leu Asp Thr Gln Lys Glu Leu Leu Glu Glu
605                 610                 615                 620 atg tat gaa gaa aaa cta aat atc ctc aag gag tca ctg aca agt ttt    2404
Met Tyr Glu Glu Lys Leu Asn Ile Leu Lys Glu Ser Leu Thr Ser Phe
                625                 630                 635 tac caa gaa gag att cag gag cgg gat gaa aag att gaa gag cta gaa    2452
Tyr Gln Glu Glu Ile Gln Glu Arg Asp Glu Lys Ile Glu Glu Leu Glu
                640                 645                 650 gct ctc ttg cag gaa gcc aga caa cag tca gtg gcc cat cag caa tca    2500
Ala Leu Leu Gln Glu Ala Arg Gln Gln Ser Val Ala His Gln Gln Ser
                655                 660                 665 ggg tct gaa ttg gcc cta cgg cgg tca caa agg ttg gca gct tct gcc    2548
Gly Ser Glu Leu Ala Leu Arg Arg Ser Gln Arg Leu Ala Ala Ser Ala
670                 675                 680 tcc acc cag cag ctt cag gag gtt aaa gct aaa tta cag cag tgc aaa    2596
Ser Thr Gln Gln Leu Gln Glu Val Lys Ala Lys Leu Gln Gln Cys Lys
685                 690                 695                 700 gca gag cta aac tct acc act gaa gag ttg cat aag tat cag aaa atg    2644
Ala Glu Leu Asn Ser Thr Thr Glu Glu Leu His Lys Tyr Gln Lys Met
                705                 710                 715 tta gaa cca cca ccc tca gcc aag ccc ttc acc att gat gtg gac aag    2692
Leu Glu Pro Pro Pro Ser Ala Lys Pro Phe Thr Ile Asp Val Asp Lys
                720                 725                 730 aag tta gaa gag ggc cag aag aat ata agg ctg ttg cgg aca gag ctt    2740
Lys Leu Glu Glu Gly Gln Lys Asn Ile Arg Leu Leu Arg Thr Glu Leu
                735                 740                 745 cag aaa ctt ggt gag tct ctc caa tca gca gag aga gct tgt tgc cac    2788
Gln Lys Leu Gly Glu Ser Leu Gln Ser Ala Glu Arg Ala Cys Cys His
                750                 755                 760
```

-continued

```
agc act ggg gca gga aaa ctt cgt caa gcc ttg acc act tgt gat gac    2836
Ser Thr Gly Ala Gly Lys Leu Arg Gln Ala Leu Thr Thr Cys Asp Asp
765                 770                 775                 780 atc tta atc aaa cag gac cag act ctg gct gaa ctg cag aac aac atg    2884
Ile Leu Ile Lys Gln Asp Gln Thr Leu Ala Glu Leu Gln Asn Asn Met
            785                 790                 795 gtg cta gtg aaa ctg gac ctt cgg aag aag gca gca tgt att gct gag    2932
Val Leu Val Lys Leu Asp Leu Arg Lys Lys Ala Ala Cys Ile Ala Glu
        800                 805                 810 cag tat cat act gtg ttg aaa ctc caa ggc cag gtt tct gcc aaa aag    2980
Gln Tyr His Thr Val Leu Lys Leu Gln Gly Gln Val Ser Ala Lys Lys
    815                 820                 825 cgc ctt ggt acc aac cag gaa aat cag caa cca aac caa caa cca cca    3028
Arg Leu Gly Thr Asn Gln Glu Asn Gln Gln Pro Asn Gln Gln Pro Pro
830                 835                 840 ggg aag aaa cca ttc ctt cga aat tta ctt ccc cga aca cca acc tgc    3076
Gly Lys Lys Pro Phe Leu Arg Asn Leu Leu Pro Arg Thr Pro Thr Cys
845                 850                 855                 860 caa agc tca aca gac tgc agc cct tat gcc cgg atc cta cgc tca cgg    3124
Gln Ser Ser Thr Asp Cys Ser Pro Tyr Ala Arg Ile Leu Arg Ser Arg
            865                 870                 875 cgt tcc cct tta ctc aaa tct ggg cct ttt ggc aaa aag tac taa        3169
Arg Ser Pro Leu Leu Lys Ser Gly Pro Phe Gly Lys Lys Tyr
        880                 885                 890 ggctgtgggg aaagagaaga gcagtcatgg ccctgaggtg ggtcagctac tctcctgaag  3229
aaataggtct cttttatgct ttaccatata tcaggaatta tatccaggat gcaatactca  3289
gacactagct ttttctcac ttttgtatta taaccaccta tgtaatctca tgttgttgtt   3349 ttttttatt tacttatatg atttctatgc acacaaaaac agttatatta aagatattat   3409
tgttcacatt ttttattgaa ttccaaatgt agcaaaatca ttaaaacaaa ttataaaagg  3469
ga                                                                 3471

<210> SEQ ID NO 2
<211> LENGTH: 890
<212> TYPE: PRT
<213> ORGANISM: Homo sapiens

<400> SEQUENCE: 2

Met Ser Gln Gly Ile Leu Ser Pro Ala Gly Leu Leu Ser Asp Asp
1               5                   10                  15

Asp Val Val Ser Pro Met Phe Glu Ser Thr Ala Ala Asp Leu Gly
            20                  25                  30

Ser Val Val Arg Lys Asn Leu Leu Ser Asp Cys Ser Val Val Ser Thr
            35                  40                  45

Ser Leu Glu Asp Lys Gln Gln Val Pro Ser Glu Asp Ser Met Glu Lys
        50                  55                  60

Val Lys Val Tyr Leu Arg Val Arg Pro Leu Leu Pro Ser Glu Leu Glu
65                  70                  75                  80

Arg Gln Glu Asp Gln Gly Cys Val Arg Ile Glu Asn Val Glu Thr Leu
                85                  90                  95

Val Leu Gln Ala Pro Lys Asp Ser Phe Ala Leu Lys Ser Asn Glu Arg
            100                 105                 110

Gly Ile Gly Gln Ala Thr His Arg Phe Thr Phe Ser Gln Ile Phe Gly
        115                 120                 125

Pro Glu Val Gly Gln Ala Ser Phe Phe Asn Leu Thr Val Lys Glu Met
    130                 135                 140
```

-continued

Val Lys Asp Val Leu Lys Gly Gln Asn Trp Leu Ile Tyr Thr Tyr Gly
145                 150                 155                 160

Val Thr Asn Ser Gly Lys Thr His Thr Ile Gln Gly Thr Ile Lys Asp
            165                 170                 175

Gly Gly Ile Leu Pro Arg Ser Leu Ala Leu Ile Phe Asn Ser Leu Gln
        180                 185                 190

Gly Gln Leu His Pro Thr Pro Asp Leu Lys Pro Leu Leu Ser Asn Glu
    195                 200                 205

Val Ile Trp Leu Asp Ser Lys Gln Ile Arg Gln Glu Glu Met Lys Lys
210                 215                 220

Leu Ser Leu Leu Asn Gly Gly Leu Gln Glu Glu Leu Ser Thr Ser
225                 230                 235                 240

Leu Lys Arg Ser Val Tyr Ile Glu Ser Arg Ile Gly Thr Ser Thr Ser
                245                 250                 255

Phe Asp Ser Gly Ile Ala Gly Leu Ser Ser Ile Ser Gln Cys Thr Ser
            260                 265                 270

Ser Ser Gln Leu Asp Glu Thr Ser His Arg Trp Ala Gln Pro Asp Thr
        275                 280                 285

Ala Pro Leu Pro Val Pro Ala Asn Ile Arg Phe Ser Ile Trp Ile Ser
290                 295                 300

Phe Phe Glu Ile Tyr Asn Glu Leu Leu Tyr Asp Leu Leu Glu Pro Pro
305                 310                 315                 320

Ser Gln Gln Arg Lys Arg Gln Thr Leu Arg Leu Cys Glu Asp Gln Asn
                325                 330                 335

Gly Asn Pro Tyr Val Lys Asp Leu Asn Trp Ile His Val Gln Asp Ala
            340                 345                 350

Glu Glu Ala Trp Lys Leu Leu Lys Val Gly Arg Lys Asn Gln Ser Phe
        355                 360                 365

Ala Ser Thr His Leu Asn Gln Asn Ser Ser Arg Ser His Ser Ile Phe
370                 375                 380

Ser Ile Arg Ile Leu His Leu Gln Gly Glu Gly Asp Ile Val Pro Lys
385                 390                 395                 400

Ile Ser Glu Leu Ser Leu Cys Asp Leu Ala Gly Ser Glu Arg Cys Lys
                405                 410                 415

Asp Gln Lys Ser Gly Glu Arg Leu Lys Glu Ala Gly Asn Ile Asn Thr
            420                 425                 430

Ser Leu His Thr Leu Gly Arg Cys Ile Ala Ala Leu Arg Gln Asn Gln
        435                 440                 445

Gln Asn Arg Ser Lys Gln Asn Leu Val Pro Phe Arg Asp Ser Lys Leu
450                 455                 460

Thr Arg Val Phe Gln Gly Phe Phe Thr Gly Arg Gly Arg Ser Cys Met
465                 470                 475                 480

Ile Val Asn Val Asn Pro Cys Ala Ser Thr Tyr Asp Glu Thr Leu His
                485                 490                 495

Val Ala Lys Phe Ser Ala Ile Ala Ser Gln Leu Val His Ala Pro Pro
            500                 505                 510

Met Gln Leu Gly Phe Pro Ser Leu His Ser Phe Ile Lys Glu His Ser
        515                 520                 525

Leu Gln Val Ser Pro Ser Leu Glu Lys Gly Ala Lys Ala Asp Thr Gly
530                 535                 540

Leu Asp Asp Asp Ile Glu Asn Glu Ala Asp Ile Ser Met Tyr Gly Lys
545                 550                 555                 560

```
Glu Glu Leu Leu Gln Val Val Glu Ala Met Lys Thr Leu Leu Lys
                565                 570                 575
Glu Arg Gln Glu Lys Leu Gln Leu Glu Met His Leu Arg Asp Glu Ile
            580                 585                 590
Cys Asn Glu Met Val Glu Gln Met Gln Gln Arg Glu Gln Trp Cys Ser
        595                 600                 605
Glu His Leu Asp Thr Gln Lys Glu Leu Leu Glu Met Tyr Glu Glu
    610                 615                 620
Lys Leu Asn Ile Leu Lys Glu Ser Leu Thr Ser Phe Tyr Gln Glu Glu
625                 630                 635                 640
Ile Gln Glu Arg Asp Lys Ile Glu Glu Leu Glu Ala Leu Leu Gln
                645                 650                 655
Glu Ala Arg Gln Gln Ser Val Ala His Gln Ser Gly Ser Glu Leu
            660                 665                 670
Ala Leu Arg Arg Ser Gln Arg Leu Ala Ala Ser Ala Ser Thr Gln Gln
        675                 680                 685
Leu Gln Glu Val Lys Ala Lys Leu Gln Gln Cys Lys Ala Glu Leu Asn
    690                 695                 700
Ser Thr Thr Glu Glu Leu His Lys Tyr Gln Lys Met Leu Glu Pro Pro
705                 710                 715                 720
Pro Ser Ala Lys Pro Phe Thr Ile Asp Val Asp Lys Lys Leu Glu Glu
                725                 730                 735
Gly Gln Lys Asn Ile Arg Leu Leu Arg Thr Glu Leu Gln Lys Leu Gly
            740                 745                 750
Glu Ser Leu Gln Ser Ala Glu Arg Ala Cys Cys His Ser Thr Gly Ala
        755                 760                 765
Gly Lys Leu Arg Gln Ala Leu Thr Thr Cys Asp Ile Leu Ile Lys
    770                 775                 780
Gln Asp Gln Thr Leu Ala Glu Leu Gln Asn Asn Met Val Leu Val Lys
785                 790                 795                 800
Leu Asp Leu Arg Lys Lys Ala Ala Cys Ile Ala Glu Gln Tyr His Thr
                805                 810                 815
Val Leu Lys Leu Gln Gly Gln Val Ser Ala Lys Lys Arg Leu Gly Thr
            820                 825                 830
Asn Gln Glu Asn Gln Gln Pro Asn Gln Gln Pro Gly Lys Lys Pro
        835                 840                 845
Phe Leu Arg Asn Leu Leu Pro Arg Thr Pro Thr Cys Gln Ser Ser Thr
    850                 855                 860
Asp Cys Ser Pro Tyr Ala Arg Ile Leu Arg Ser Arg Ser Pro Leu
865                 870                 875                 880
Leu Lys Ser Gly Pro Phe Gly Lys Lys Tyr
                885                 890

<210> SEQ ID NO 3
<211> LENGTH: 9
<212> TYPE: PRT
<213> ORGANISM: Artificial Sequence
<220> FEATURE:
<223> OTHER INFORMATION: A peptide sequence derived from human RAB6KIFL

<400> SEQUENCE: 3

Leu Leu Ser Asp Asp Val Val Val
1               5
```

-continued

```
<210> SEQ ID NO 4
<211> LENGTH: 9
<212> TYPE: PRT
<213> ORGANISM: Artificial Sequence
<220> FEATURE:
<223> OTHER INFORMATION: A peptide sequence derived from human RAB6KIFL

<400> SEQUENCE: 4

Cys Ile Ala Glu Gln Tyr His Thr Val
1               5

<210> SEQ ID NO 5
<211> LENGTH: 10
<212> TYPE: PRT
<213> ORGANISM: Artificial Sequence
<220> FEATURE:
<223> OTHER INFORMATION: A peptide sequence derived from human RAB6KIFL

<400> SEQUENCE: 5

Ala Gln Pro Asp Thr Ala Pro Leu Pro Val
1               5                   10

<210> SEQ ID NO 6
<211> LENGTH: 21
<212> TYPE: DNA
<213> ORGANISM: Artificial
<220> FEATURE:
<223> OTHER INFORMATION: An artificially synthesized primer for PCR

<400> SEQUENCE: 6
ctacaagcac ccaaggactc t                                                21

<210> SEQ ID NO 7
<211> LENGTH: 20
<212> TYPE: DNA
<213> ORGANISM: Artificial
<220> FEATURE:
<223> OTHER INFORMATION: An artificially synthesized primer for PCR

<400> SEQUENCE: 7
agatggagaa gcgaatgttt                                                  20

<210> SEQ ID NO 8
<211> LENGTH: 23
<212> TYPE: DNA
<213> ORGANISM: Artificial
<220> FEATURE:
<223> OTHER INFORMATION: An artificially synthesized primer for PCR

<400> SEQUENCE: 8
catccacgaa actaccttca act                                              23

<210> SEQ ID NO 9
<211> LENGTH: 23
<212> TYPE: DNA
<213> ORGANISM: Artificial
<220> FEATURE:
<223> OTHER INFORMATION: An artificially synthesized primer for PCR

<400> SEQUENCE: 9
tctccttaga gagaagtggg gtg                                              23

<210> SEQ ID NO 10
<211> LENGTH: 9
<212> TYPE: PRT
<213> ORGANISM: Artificial
```

```
<220> FEATURE:
<223> OTHER INFORMATION: A peptide sequence derived from HIV

<400> SEQUENCE: 10

Ser Leu Tyr Asn Thr Tyr Ala Thr Leu
1               5

<210> SEQ ID NO 11
<211> LENGTH: 9
<212> TYPE: PRT
<213> ORGANISM: mouse

<400> SEQUENCE: 11

Leu Leu Ser Asp Glu Asp Val Val Asp
1               5

<210> SEQ ID NO 12
<211> LENGTH: 10
<212> TYPE: PRT
<213> ORGANISM: mouse

<400> SEQUENCE: 12

Ala Gln Pro Asp Thr Val Pro Val Ser Val
1               5                   10
```